United States Patent
Midorikawa

(10) Patent No.: US 10,751,168 B2
(45) Date of Patent: Aug. 25, 2020

(54) INTRAOCULAR LENS INSERTION APPARATUS

(71) Applicant: KOWA COMPANY, LTD., Nagoya-shi, Aichi (JP)

(72) Inventor: Genyo Midorikawa, Nagoya (JP)

(73) Assignee: KOWA COMPANY, LTD., Nagoya-Shi, Aichi ( * ) Notice: Subject to any disclaimer, the term of this patent is extended or adjusted under 35 U.S.C. 154(b) by 368 days.

(21) Appl. No.: 15/567,053

(22) PCT Filed: Jan. 20, 2016

(86) PCT No.: PCT/JP2016/051589
§ 371 (c)(1),
(2) Date: Oct. 16, 2017

(87) PCT Pub. No.: WO2016/167000
PCT Pub. Date: Oct. 20, 2016

(65) Prior Publication Data
US 2018/0098842 A1  Apr. 12, 2018

(30) Foreign Application Priority Data

Apr. 17, 2015  (JP) ................................. 2015-085353

(51) Int. Cl.
*A61F 2/16* (2006.01)
*A61M 5/31* (2006.01)
*A61M 5/315* (2006.01)

(52) U.S. Cl.
CPC ............ *A61F 2/1678* (2013.01); *A61F 2/167* (2013.01); *A61F 2/1667* (2013.01); *A61F 2/1675* (2013.01);
(Continued)

(58) Field of Classification Search
CPC ...... A61F 2/1667; A61F 2/1662; A61F 2/167; A61F 2/1672; A61F 2/1678;
(Continued)

(56) References Cited

U.S. PATENT DOCUMENTS 3,729,032 A * 4/1973 Tischlinger ......... A61M 5/1782
141/2
6,126,644 A 10/2000 Naganuma et al.
(Continued)

FOREIGN PATENT DOCUMENTS

EP   0 845 275 A2   6/1998
EP   1 123 712 A1   8/2001
(Continued)

OTHER PUBLICATIONS

First Office Action in corresponding Chinese Patent Application No. 201680022380.6, dated Sep. 14, 2018.
(Continued)

*Primary Examiner* — Ashley L Fishback
(74) *Attorney, Agent, or Firm* — Knobbe, Martens, Olson & Bear LLP

(57) ABSTRACT

An intraocular lens insertion apparatus includes an apparatus body configured to include a housing member for housing an intraocular lens and an insertion tube member for ejecting the intraocular lens into an eyeball of a patient, a plunger configured to move in the apparatus body, and a hook member formed on the apparatus body for a user of the intraocular lens insertion apparatus to hook a finger when the user moves the plunger. The plunger is moved to a side of the insertion tube member, the intraocular lens housed in the housing member is pushed by a distal end of the plunger, and the intraocular lens is ejected from the insertion tube member, and a connecting member configured to connect an operability enhancing member for enhancing an operability
(Continued)

of the plunger when the plunger is moved with the apparatus body is provided for the apparatus body.

13 Claims, 18 Drawing Sheets

(52) U.S. Cl.
CPC . *A61F 2002/1681* (2013.01); *A61F 2250/009* (2013.01); *A61M 5/315* (2013.01); *A61M 5/3137* (2013.01); *A61M 5/31501* (2013.01)

(58) Field of Classification Search
CPC .......... A61F 2/1675; A61F 2002/1681; A61M 5/3137; A61M 5/315; A61M 5/31501; A61M 5/31505
See application file for complete search history.

(56) References Cited

U.S. PATENT DOCUMENTS

| | | | |
|---|---|---|---|
| 2001/0007075 A1* | 7/2001 | Hjertman | A61F 2/1667 606/107 |
| 2001/0021823 A1 | 9/2001 | Nemoto | |
| 2004/0082919 A1 | 4/2004 | Nemoto | |
| 2004/0087908 A1 | 5/2004 | Nemoto | |
| 2004/0087909 A1 | 5/2004 | Nemoto | |
| 2004/0087910 A1 | 5/2004 | Nemoto | |
| 2004/0092881 A1 | 5/2004 | Nemoto | |
| 2008/0132845 A1 | 6/2008 | Nemoto | |
| 2008/0132853 A1 | 6/2008 | Nemoto | |
| 2008/0221584 A1 | 9/2008 | Downer | |
| 2009/0005788 A1 | 1/2009 | Rathert | |
| 2013/0310843 A1 | 11/2013 | Brown | |
| 2013/0331853 A1 | 12/2013 | Marunaka et al. | |

FOREIGN PATENT DOCUMENTS

| | | |
|---|---|---|
| EP | 2 641 568 A1 | 9/2013 |
| JP | 2002-011096 A | 1/2002 |
| JP | 2004-261263 A | 9/2004 |
| JP | 2005-328869 A | 12/2005 |
| JP | 2007-089731 A | 4/2007 |
| JP | 2008-212219 A | 9/2008 |
| JP | 2008-212689 A | 9/2008 |
| JP | 2008-272084 A | 11/2008 |
| JP | 2008-272257 A | 11/2008 |
| JP | 2012-125361 A | 7/2012 |
| JP | 2013-048662 A | 3/2013 |
| JP | 2013-180130 A | 9/2013 |
| JP | 2014-050484 A | 3/2014 |
| JP | 3191075 U | 6/2014 |

OTHER PUBLICATIONS

International Search Report for International Application No. PCT/JP2016/051589, dated Mar. 22, 2016.

Extended European Search Report received in European Patent Application No. 16779792.7 dated Nov. 13, 2018.

* cited by examiner

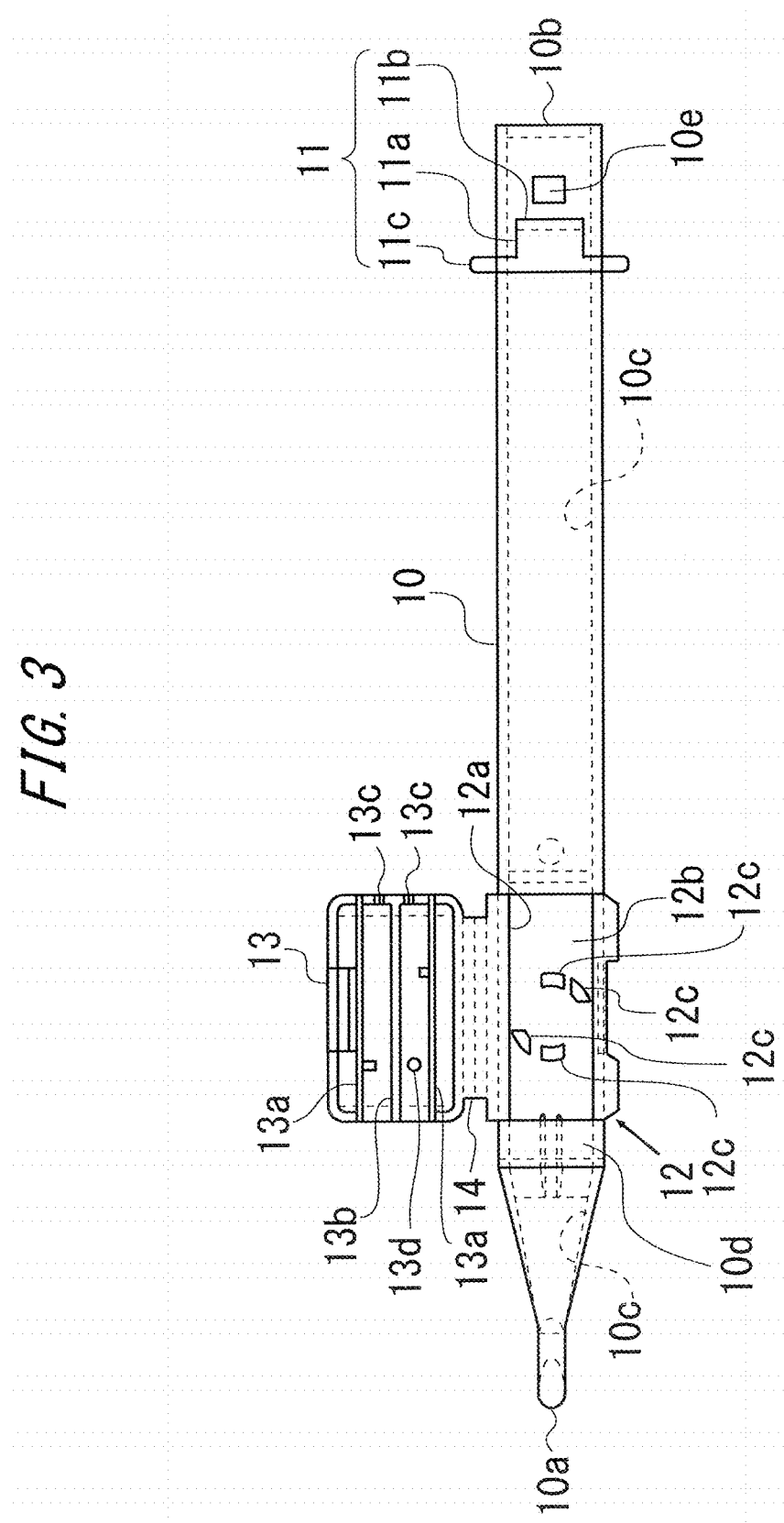

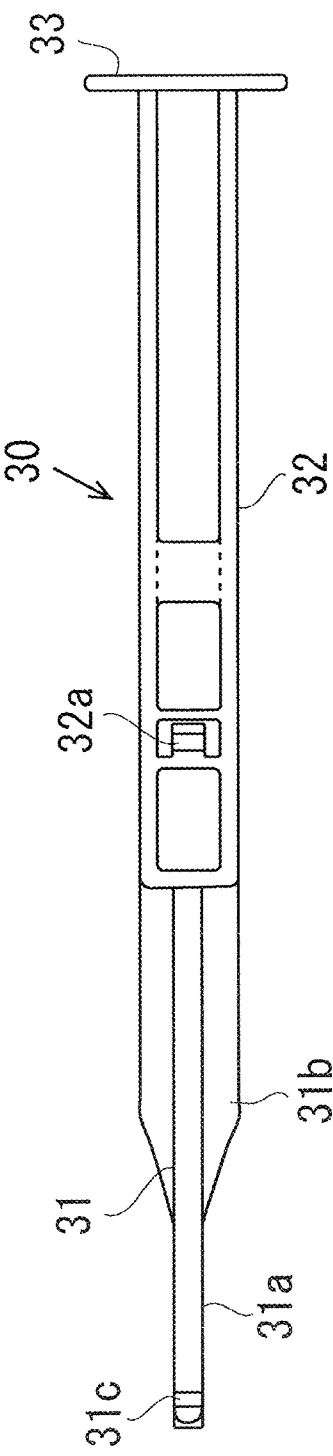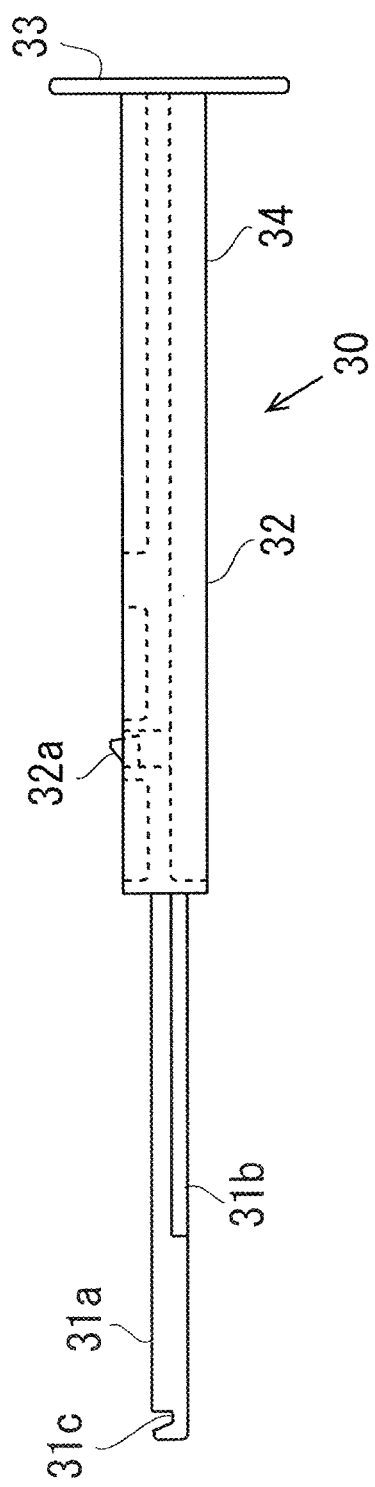
FIG. 5A
FIG. 5B

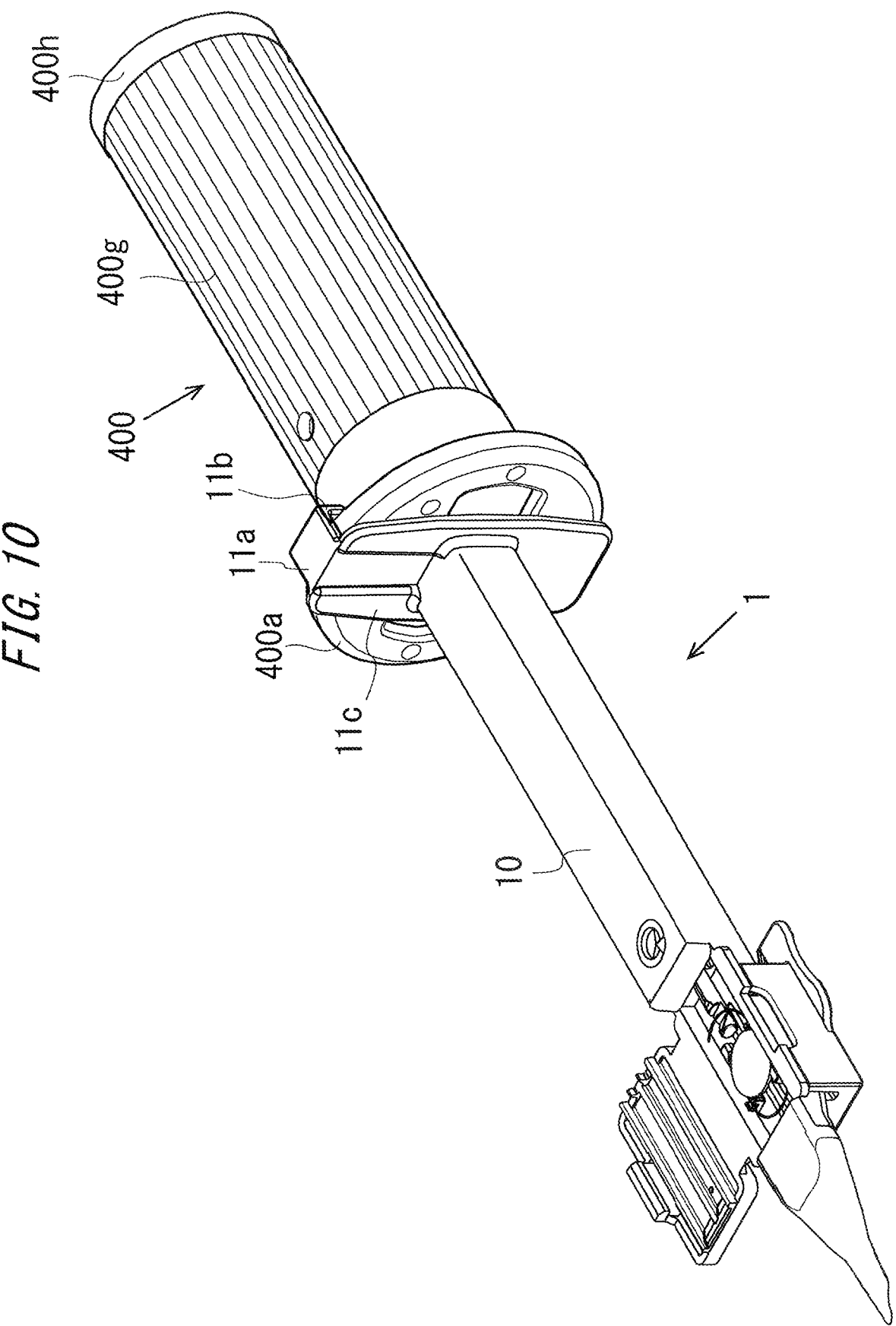

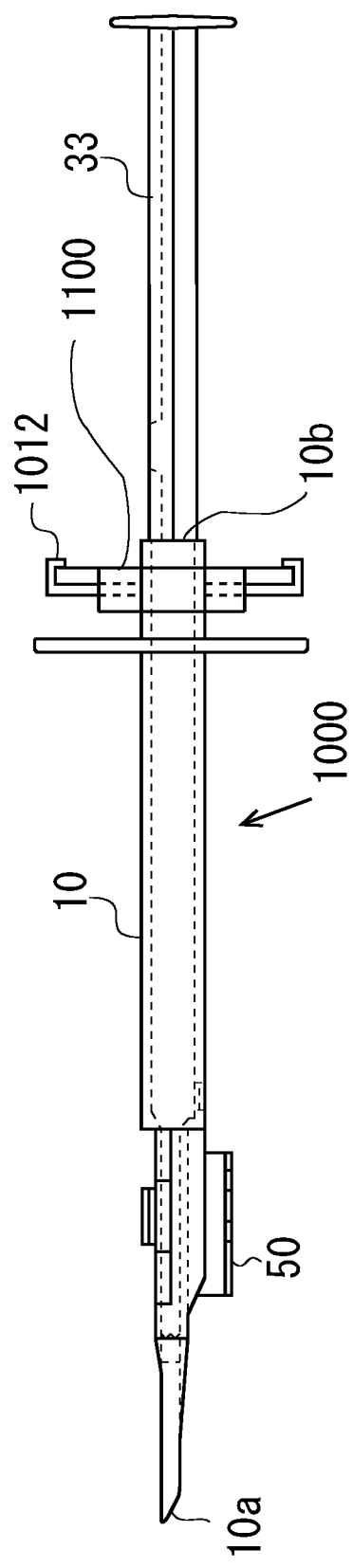
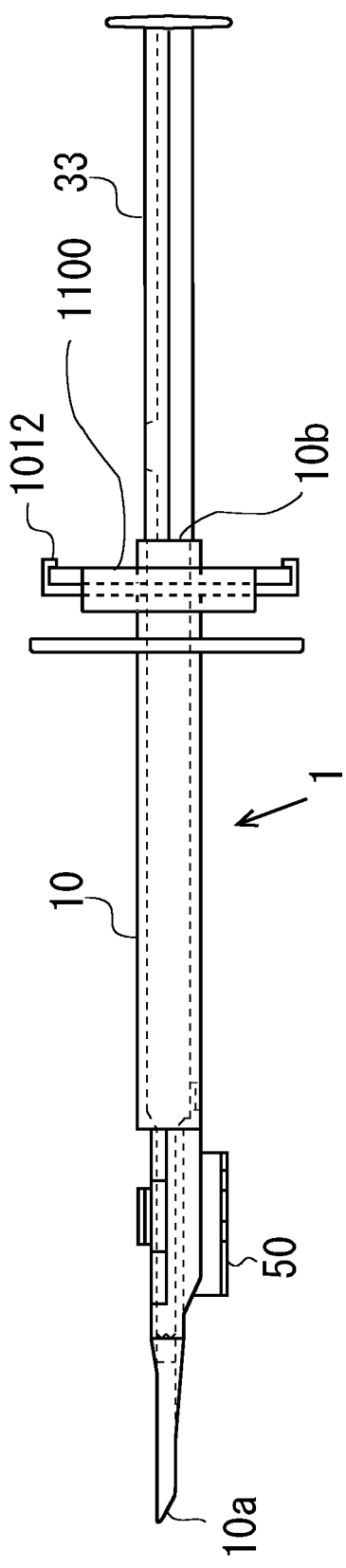

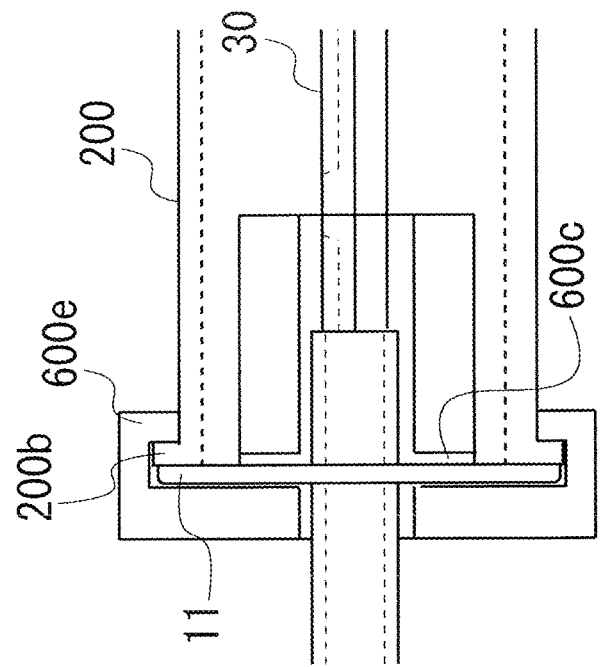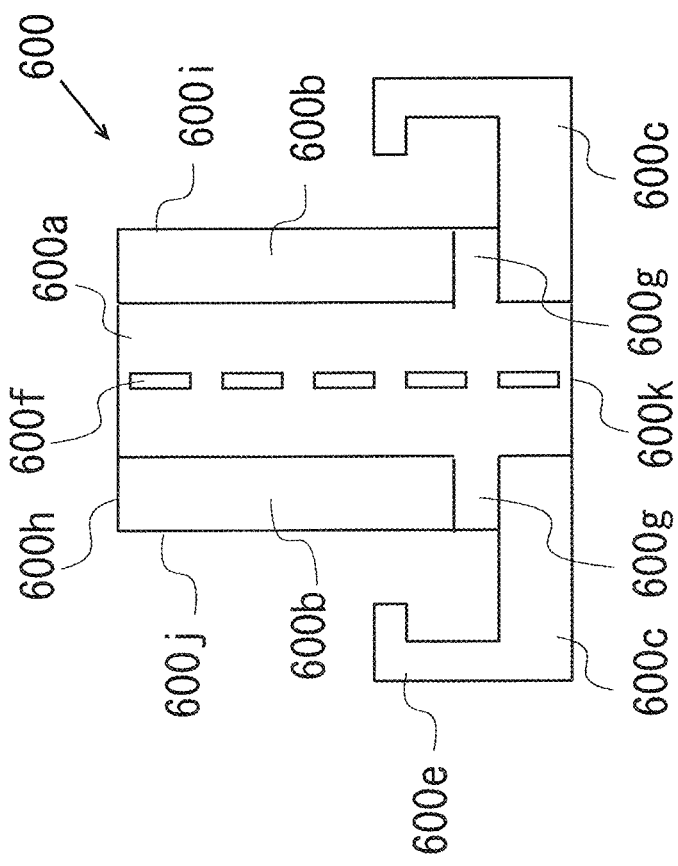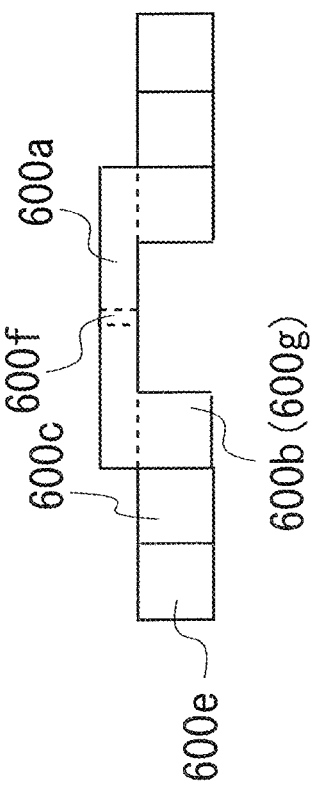

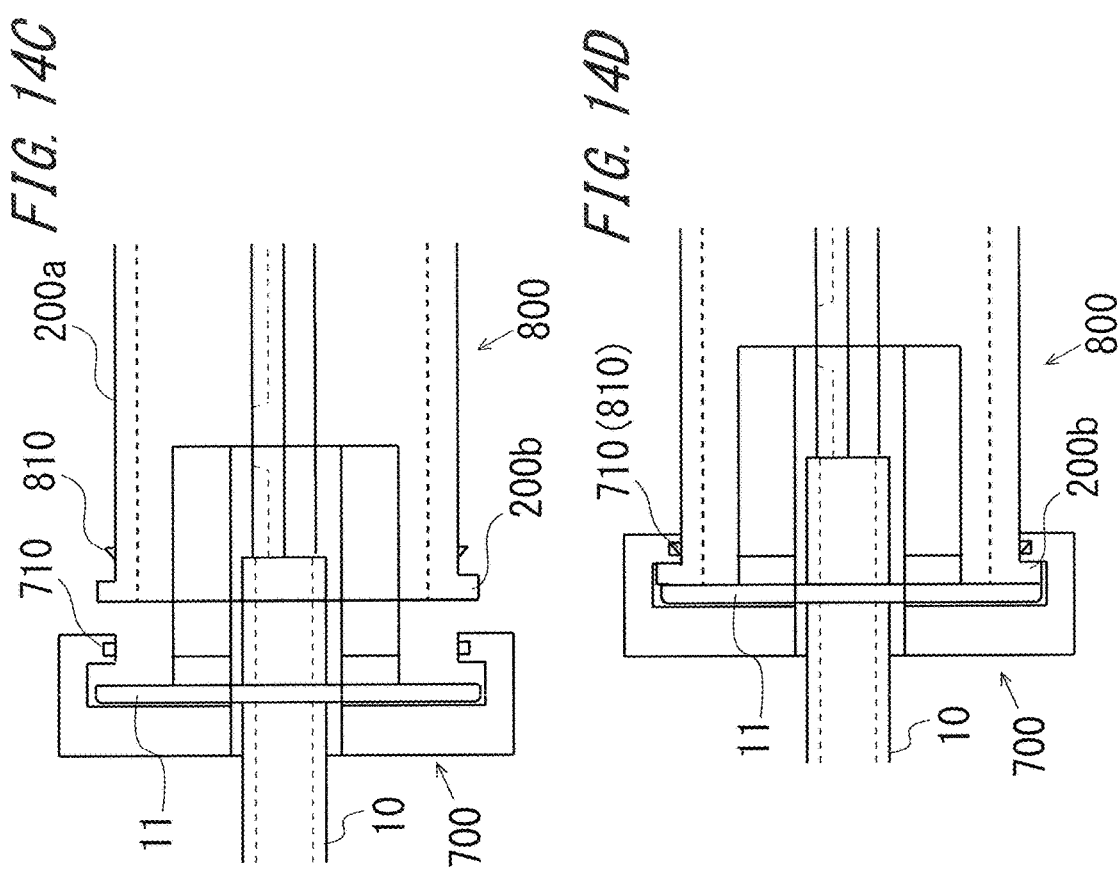
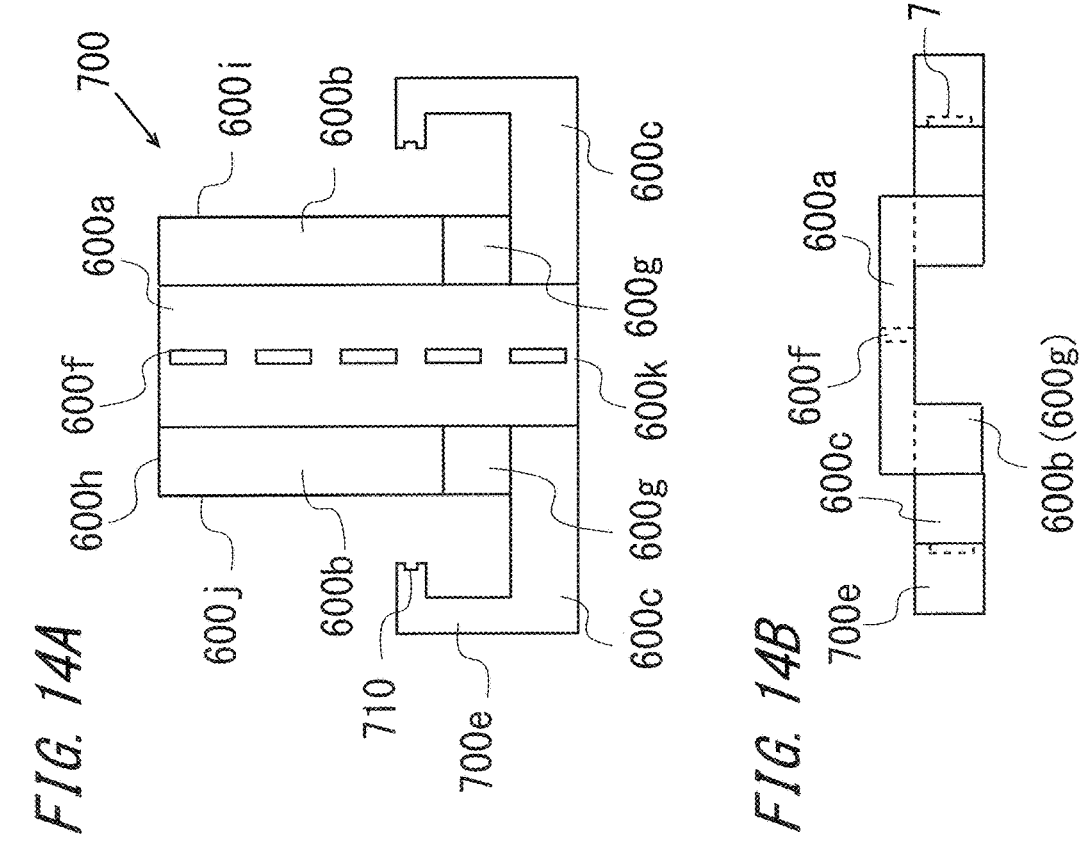

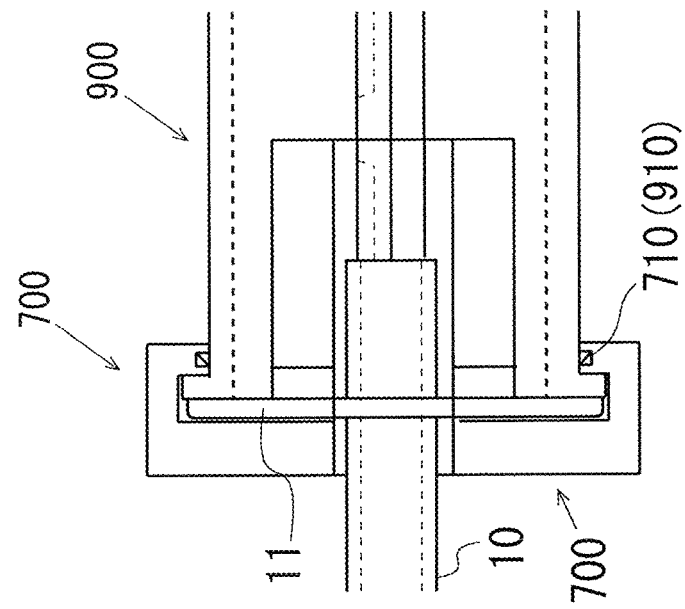
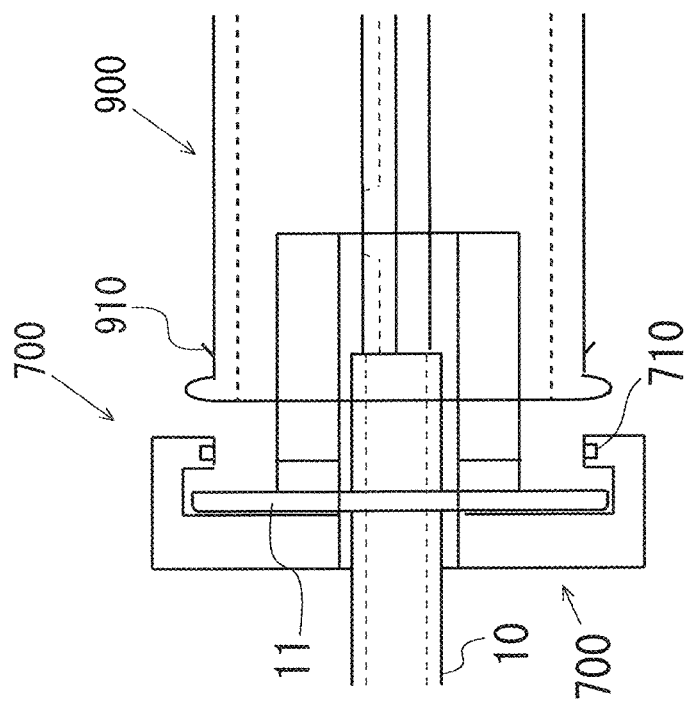

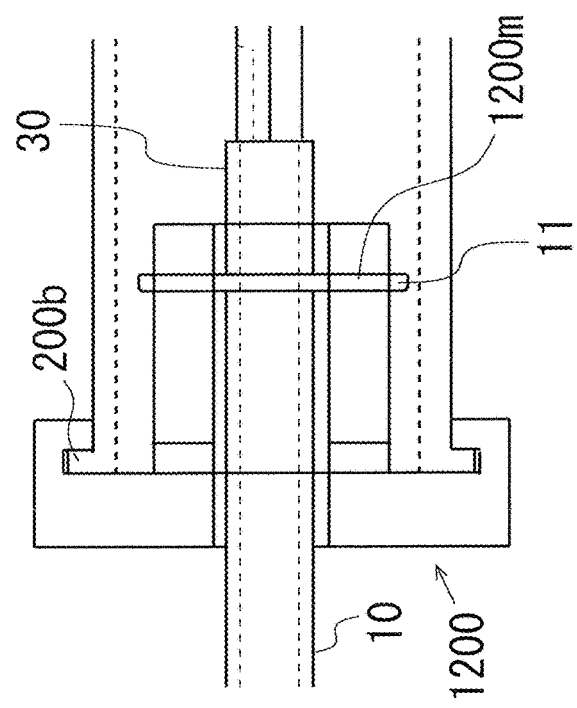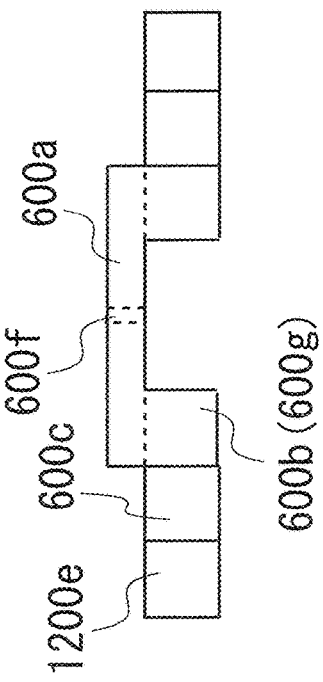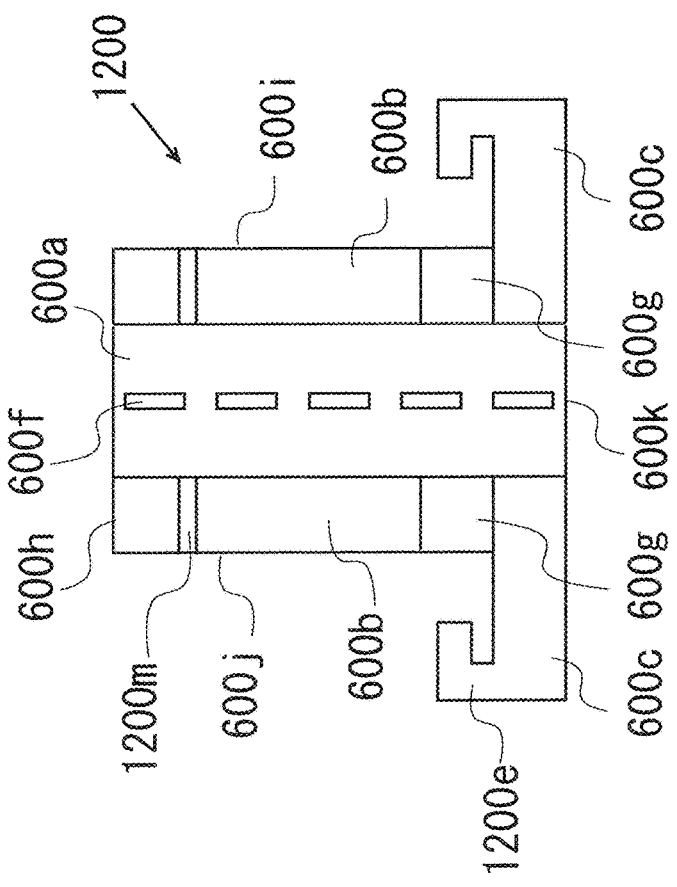

INTRAOCULAR LENS INSERTION APPARATUS

FIELD

The embodiments discussed herein relate to an intraocular lens insertion apparatus.

BACKGROUND

Intraocular lenses are widely used to be replaced with human opacity crystalline lenses in cataract treatments to compensate the optical powers of the lenses. In intraocular lens insertion surgeries for the cataract treatments, an incision (discission cut) which is several millimeters in length is produced at the edge of the cornea or the sclerocornea, the human crystalline lens is crushed and removed by phacoemulsification and aspiration etc. and the intraocular lens is inserted and fixed in the eye using an intraocular lens insertion apparatus, for example. Recently, techniques for supporting the insertion of an intraocular lens into an eyeball of a patient by using an intraocular lens insertion apparatus are proposed (See Patent Literatures 1, 2 and 3).

CITATION LIST

Patent Literature

[PTL 1] JP-A-2014-050484
[PTL 2] JP-A-2008-272257
[PTL 3] JP-A-2004-261263

SUMMARY

Technical Problem

A conventional intraocular lens insertion apparatus employs a plunger to push an intraocular lens housed in an intraocular lens housing member of the apparatus body. The plunger moves the intraocular lens in the apparatus body and the intraocular lens is ejected into an eyeball of a patient. A user of the apparatus hooks his fingers onto a hook member of the apparatus body and uses another finger to push the plunger toward the apparatus body to eject the intraocular lens into the eyeball.

However, the size of the hook member of the apparatus body of the conventional intraocular lens insertion apparatus may not be configured to be enough large for the user's operation in view of saving the space for the transportation and/or the storage of the apparatus. In addition, when the user uses the plunger to eject the intraocular lens into the eyeball from the apparatus body, the resistance force which the plunger receives from the intraocular lens is decreased instantaneously. Therefore, if the user does not relax the pressure of his finger pushing the plunger, the plunger may shoot from the apparatus body. Further, the plunger may move in the apparatus body due to unexpected force applied to the plunger during the transportation of the intraocular lens insertion. In this case, the intraocular lens may be moved from the normal position to an abnormal position in the apparatus body, which is undesirable.

The technique of this disclosure has been made in view of the above-mentioned circumstances, and it is an object of this disclosure to provide an intraocular lens insertion apparatus of which the operability of the plunger can be enhanced.

Solution to Problem

According to the embodiments described herein, it is provided an intraocular lens insertion apparatus including an apparatus body configured to include a housing member for housing an intraocular lens and an insertion tube member for ejecting the intraocular lens into an eyeball of a patient, a plunger configured to move in the apparatus body, and a hook member formed on the apparatus body for a user of the intraocular lens insertion apparatus to hook a finger when the user moves the plunger. The plunger is moved to a side of the insertion tube member, the intraocular lens housed in the housing member is pushed by a distal end of the plunger, and the intraocular lens is ejected from the insertion tube member, and a connecting member configured to connect an operability enhancing member for enhancing an operability of the plunger when the plunger is moved with the apparatus body is provided for the apparatus body. With such configuration, when the member for enhancing the operability of the plunger is connected with the apparatus body, an operability which is appropriate for the user's medical procedure using the plunger can be achieved. As a result, the possibility that the plunger shoots from the apparatus body can be decreased when the intraocular lens is ejected from the apparatus body and the counteracting force applied to the plunger from the intraocular lens pushed by the plunger momentarily becomes small. In addition, the connecting member can be provided for the hook member.

Further, the hook member can be formed on the apparatus body and a shape of a part of the hook member is configured to be a plate which is perpendicular to a direction of movement of the plunger, and the connecting member can include a collar member formed on the hook member, the collar member can be formed on a side opposite to a side facing the insertion tube member, and the collar member can be configured to connect with a flange provided for the operability enhancing member. The connecting member can be integrally formed on the hook member. The connecting member can be detachably formed on the hook member. The operability enhancing member can be connected to the connecting member from a rear end side of the apparatus body. The operability enhancing member can be configured to connect with connecting member to prevent the direction of movement of the plunger from tilting when the user moves the plunger.

Additionally, the operability enhancing member can be a plate member configured to increase an area of the hook member onto which the user hooks the finger to move the plunger when the plate member is connected with the connecting member. The operability enhancing member can include a wall which projects from the rear end of the hook member and beyond the rear end of the apparatus body in a direction opposite to the direction of the movement of the plunger. The operability enhancing member can include a tube member which extends from the rear end of the hook member in a direction opposite to the direction of the movement of the plunger to cover the plunger. The operability enhancing member can include a motion conversion device which is configured to covert a rotational motion of a rotating member rotated by the user to a linear motion and which is configured to transmit the linear motion to the plunger to move in the apparatus body. The operability enhancing member can include a driving source configured to move the plunger. The intraocular lens can be housed in the insertion tube member before the intraocular lens insertion apparatus is distributed.

In addition, it is provided an intraocular lens insertion apparatus which includes an apparatus body configured to include a housing member for housing an intraocular lens and an insertion tube member for ejecting the intraocular lens into an eyeball of a patient, a plunger configured to move in the apparatus body, and a hook member formed on the apparatus body for a user of the intraocular lens insertion apparatus to hook a finger when the user moves the plunger. The plunger is moved to a side of the insertion tube member, the intraocular lens housed in the housing member is pushed by a distal end of the plunger, and the intraocular lens is ejected from the insertion tube member, the intraocular lens insertion apparatus further includes a connecting member configured to connect an operability enhancing member for enhancing an operability of the plunger when the plunger is moved with the apparatus body, and the connecting member comprises a detachment prevention mechanism configured to prevent the operability enhancing member and the apparatus body from detaching from the connecting member after the operability enhancing member and the apparatus body are attached to the connecting member.

Further, it is provided an intraocular lens insertion apparatus which includes an apparatus body configured to include a housing member for housing an intraocular lens and an insertion tube member for ejecting the intraocular lens into an eyeball of a patient, a plunger configured to move in the apparatus body, and a hook member formed on the apparatus body for a user of the intraocular lens insertion apparatus to hook a finger when the user moves the plunger. The plunger is moved to a side of the insertion tube member, the intraocular lens housed in the housing member is pushed by a distal end of the plunger, and the intraocular lens is ejected from the insertion tube member, the intraocular lens insertion apparatus further includes a connecting member configured to connect an operability enhancing member to the body for enhancing the operability of the plunger when the plunger is moved with the apparatus body, the connecting member includes a first attaching member to which an operability enhancing member for enhancing an operability of the plunger when the plunger is moved is attached and a second attaching member to which the hook member is attached, and the first attaching member is located closer to the distal end of the apparatus body than the second attaching member when the connecting member is attached to the intraocular lens insertion apparatus.

Moreover, it is provided for a connecting member which can be attached to an intraocular lens insertion apparatus. In addition, The intraocular lens insertion apparatus includes an apparatus body configured to include a housing member for housing an intraocular lens and an insertion tube member for ejecting the intraocular lens into an eyeball of a patient, a plunger configured to move in the apparatus body, and a hook member formed on the apparatus body for a user of the intraocular lens insertion apparatus to hook a finger when the user moves the plunger. The plunger is moved to a side of the insertion tube member, the intraocular lens housed in the housing member is pushed by a distal end of the plunger, and the intraocular lens is ejected from the insertion tube member, the apparatus body and an operability enhancing member for enhancing an operability of the plunger when the plunger is moved are connected with the connecting member, and the connecting member further includes a detachment prevention mechanism configured to prevent the operability enhancing member and the apparatus body from detaching from the connecting member after the operability enhancing member and the apparatus body are attached to the connecting member.

Additionally, it is provided a connecting member which can be attached to an intraocular lens insertion apparatus. In addition, the intraocular lens insertion apparatus includes an apparatus body configured to include a housing member for housing an intraocular lens and an insertion tube member for ejecting the intraocular lens into an eyeball of a patient, a plunger configured to move in the apparatus body, and a hook member formed on the apparatus body for a user of the intraocular lens insertion apparatus to hook a finger when the user moves the plunger, the plunger is moved to a side of the insertion tube member, the intraocular lens housed in the housing member is pushed by a distal end of the plunger, and the intraocular lens is ejected from the insertion tube member, the connecting member further includes a first attaching member to which the operability enhancing member is attached and a second attaching member to which the hook member is attached, and the first attaching member is located closer to the distal end of the apparatus body than the second attaching member when the connecting member is attached to the intraocular lens insertion apparatus.

Advantageous Effects of Invention

According to the technique disclosed herein, it is possible to provide an intraocular lens insertion apparatus of which the operability of the plunger can be enhanced.

BRIEF DESCRIPTION OF DRAWINGS

FIG. 3 is a diagram schematically illustrating a configuration of a nozzle body according to one embodiment.

FIG. 5A is a diagram schematically illustrating a configuration of a plunger according to one embodiment.

FIG. 5B is another diagram schematically illustrating a configuration of a plunger according to one embodiment.

FIG. 10 is a diagram schematically illustrating an operability enhancing member attached to an intraocular lens insertion apparatus.

FIG. 11A is a diagram schematically illustrating an operability enhancing member and an intraocular lens insertion apparatus according to one variation.

FIG. 11B is another diagram schematically illustrating an operability enhancing member and an intraocular lens insertion apparatus according to one variation.

FIG. 13A is a diagram schematically illustrating an intraocular lens insertion apparatus and an attaching member according to one variation.

FIG. 13B is another diagram schematically illustrating an intraocular lens insertion apparatus and an attaching member according to one variation.

FIG. 13C is yet another diagram schematically illustrating an intraocular lens insertion apparatus and an attaching member according to one variation.

FIG. 14A is a diagram schematically illustrating an intraocular lens insertion apparatus and an attaching member according to another variation.

FIG. 14B is another diagram schematically illustrating an intraocular lens insertion apparatus and an attaching member according to another variation.

FIG. 14C is yet another diagram schematically illustrating an intraocular lens insertion apparatus and an attaching member according to another variation.

FIG. 14D is still another diagram schematically illustrating an intraocular lens insertion apparatus and an attaching member according to another variation.

FIG. 15A is a diagram schematically illustrating an attaching member according to yet another variation.

FIG. 15B is another diagram schematically illustrating an attaching member according to yet another variation.

FIG. 16A is a diagram schematically illustrating an intraocular lens insertion apparatus and an attaching member according to still another variation.

FIG. 16B is another diagram schematically illustrating an intraocular lens insertion apparatus and an attaching member according to still another variation.

FIG. 16C is yet another diagram schematically illustrating an intraocular lens insertion apparatus and an attaching member according to still another variation.

DESCRIPTION OF EMBODIMENTS

Hereinafter, embodiments of the present invention are described with reference to drawings. The following descriptions of the embodiments are exemplary and do not intend that the present invention is limited to any of the embodiments.

First Embodiment

Figure 1A:
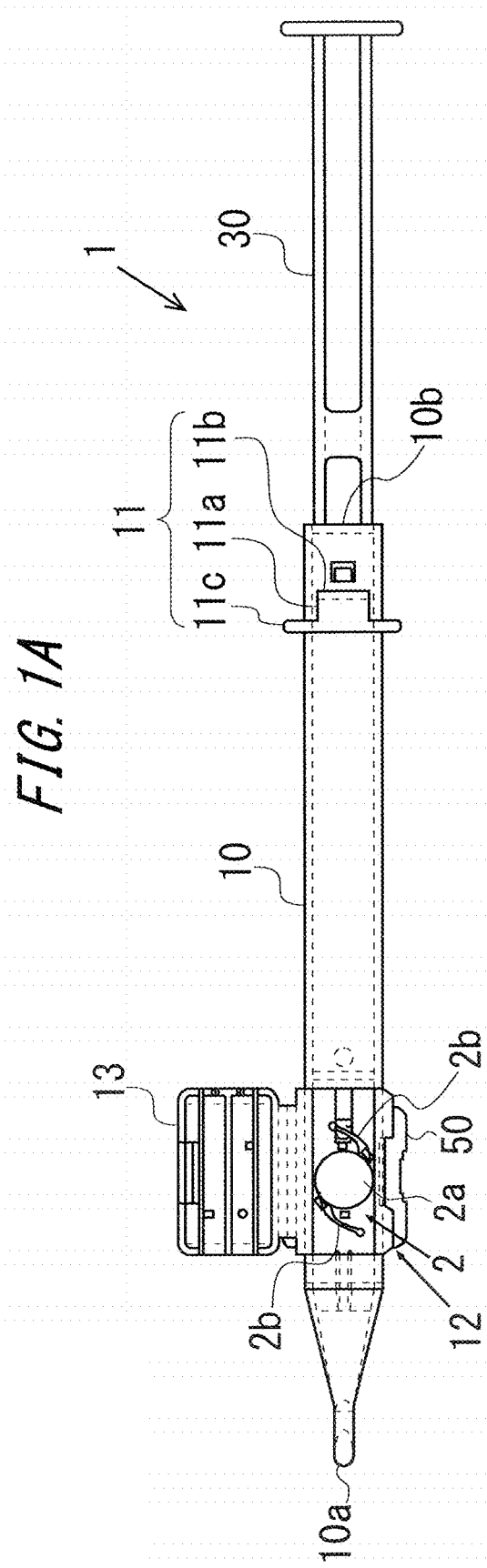
FIG. 1A is a diagram schematically illustrating a configuration of an intraocular lens insertion apparatus according to one embodiment.
Figure 1B:
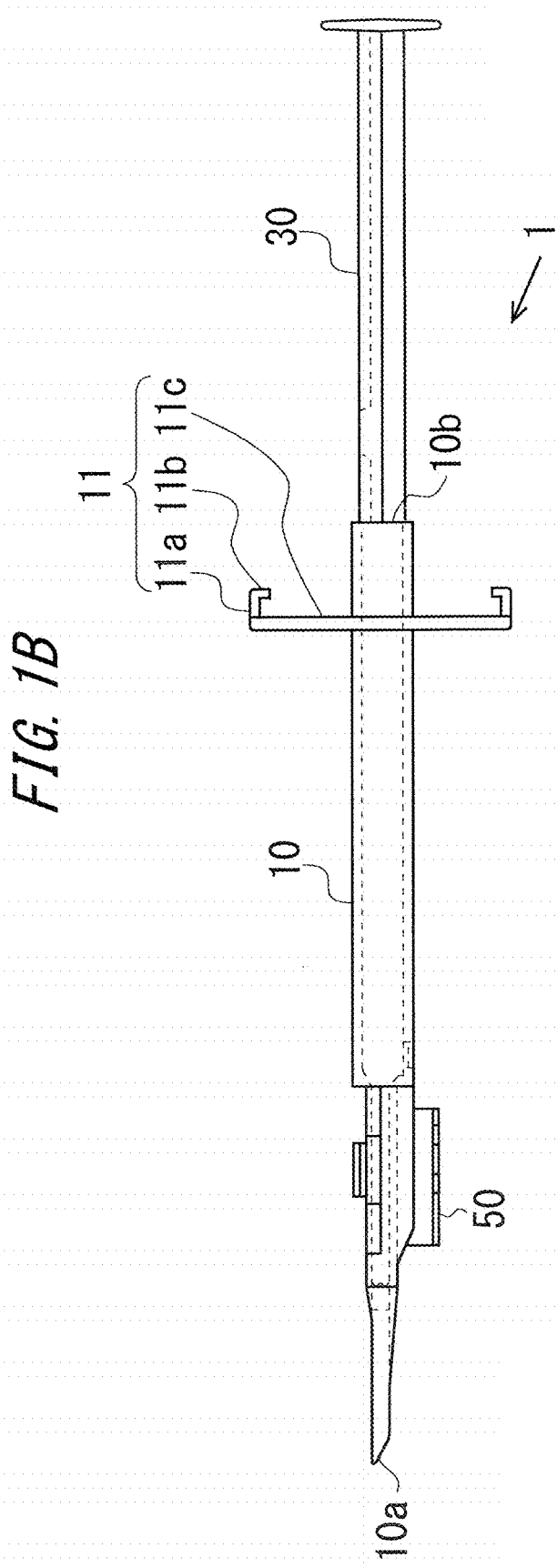
FIG. 1B is another diagram schematically illustrating a configuration of an intraocular lens insertion apparatus according to one embodiment.

FIGS. 1A and 1B schematically illustrate a configuration of an intraocular lens insertion apparatus 1 according to the first embodiment. FIG. 1A illustrates a plan view of the intraocular lens insertion apparatus 1 in a state where a stage lid member 13 is opened. FIG. 1B illustrates a side view of the intraocular lens insertion apparatus 1 in a state where the stage lid member 13 is closed. The intraocular lens insertion apparatus generally includes an apparatus body and a pushing member for pushing an intraocular lens. The apparatus body includes a nozzle body 10 and a stage member 12 and the stage lid member 13 which form an accommodating member for accommodating an intraocular lens. In addition, the pushing member for pushing the intraocular lens includes a plunger 30. The stage member 12 is integrally or independently formed on the nozzle body 10. The plunger 30 is inserted into the nozzle body 10. An intraocular lens 2 is set on the stage member 12. The stage member 12 is integrally formed with the stage lid member 13.

The nozzle body 10 of the intraocular lens insertion apparatus 1 is formed in a tubular shape the cross section of which is a rectangle. An opening formed at one end of the nozzle body 10 which is referred to as a rear end member 10b is larger than an opening formed at the other end of the nozzle body 10 which is referred to as a distal end member 10a. As illustrated in FIG. 1B, the opening of the distal end member 10a is formed into a bevel. The plunger 30 is inserted into the nozzle body 10 and can be moved to-and-fro in the nozzle body 10.

In the descriptions hereinafter, the direction extending toward the distal end member 10a from the rear end member 10b of the nozzle body 10 is assumed as the frontward direction, the direction opposite to the frontward direction is assumed as the rearward direction, the direction toward a viewer's side with respect to a paper surface on which FIG. 1A is drawn is assumed as the upward direction, the direction opposite to the upward direction is assumed as the downward direction, the direction toward a viewer's side with respect to a paper surface on which FIG. 1B is drawn is assumed as the leftward direction, and the direction opposite to the leftward direction is assumed as the rightward direction. In this case, the upward direction corresponds to a direction toward a front side along an optical axis of a lens body 2a described later, the downward direction corresponds to a direction toward a rear side along the optical axis of the lens body 2a, the frontward direction corresponds to a direction toward a front side in the pushing direction of the plunger 30, and the rearward direction corresponds to a direction toward a rear side in the pushing direction of the plunger 30.

A hold member 11 which projects in a plate shape and on which a user hooks his fingers when he pushes the plunger 30 toward the distal end side of the nozzle body 10 is integrally formed on the nozzle body 10 in the vicinity of the rear end member 10b of the nozzle body 10. The hold member 11 is an example of a hook member. As illustrated in FIGS. 1A and 1B, the hold member 11 includes a collar member 11c onto which the user hooks when the user pushes the plunger 30 toward the nozzle body 10. The collar member 11c is formed to project from the nozzle body 10 in the upward, downward, leftward and rightward directions. In the present embodiment, the length of the collar member 11c in the upward and downward directions is configured to be longer than the length of the collar member 11c in the leftward and rightward directions. Therefore, the space in the leftward and rightward directions of the intraocular lens insertion apparatus 1 when the intraocular lens insertion apparatus 1 is transported and stored can be saved.

In addition, the hold member 11 includes a plate member 11a which extends toward the posterior side of the nozzle body 10 from the edge of the collar member 11c in the upward and downward directions. Further, the hold member 11 includes engaging members 11b which extends in the upward or downward direction from the edge of the plate member 11a on the posterior side of the nozzle body 10. As illustrated in FIG. 1B, one of the engaging members 11b extends in the downward direction from the plate member 11a extending from the edge of the collar member 11c in the upward direction. In addition, the other of the engaging members 11b extends in the upward direction from the plate member 11a extending from the edge of the collar member 11c in the downward direction. Since the engaging members 11b are configured as described above, the engaging members 11b can be used as claws to connect with an operability enhancing member. It is noted that the part configured by the plate member 11a and the engaging member 11b is an example of a connecting member. Since the hold member 11 includes the plate member 11a, the engaging members 11b and the collar member 11c in the present embodiment, various additional members for enhancing the operability of the plunger can be attached to the hold member 11 from the posterior side of the nozzle body 10. The details of the various additional members are described later.

Moreover, the stage member 12 on which the intraocular lens 2 is to be set is formed on the nozzle body 10 as described above. The stage member 12 is configured such that an upper side of the nozzle body 10 is opened by opening the stage lid member 13. The positioning member 50 is mounted on the stage member 12 from below the nozzle body 10. With the use of the positioning member 50, the intraocular lens 2 is stably held on the stage member 12 even before the insertion apparatus 1 is used (during transportation).

That is, in the intraocular lens insertion apparatus 1, at the time of manufacturing the intraocular lens insertion apparatus 1, the intraocular lens 2 is set on the stage member 12 such that a front side along an optical axis is directed upward in a state where the stage lid member 13 is opened and the positioning member 50 is mounted on the stage member 12. Then, the intraocular lens insertion apparatus 1 is commercially distributed with the stage lid member 13 closed, and the intraocular lens insertion apparatus 1 is sold. Then, the user provide hyaluronic acid for the intraocular lens 2 through the insertion hole 13d of the stage lid member 13, removes the positioning member 50 while holding the stage lid member 13 in a closed state and, thereafter, pushes the plunger 30 toward the distal end side of the nozzle body 10. Due to such an operation, the intraocular lens 2 is pushed by the plunger 30, and the intraocular lens 2 is ejected into the inside of the eyeball from the distal end member 10a. In the intraocular lens insertion apparatus 1, the nozzle body 10, the plunger 30 and the positioning member 50 are formed using a resin such as polypropylene. Polypropylene has been proven as a material used for medical apparatuses. In addition, polypropylene is reliable in chemical resistance etc.

Figure 2A:
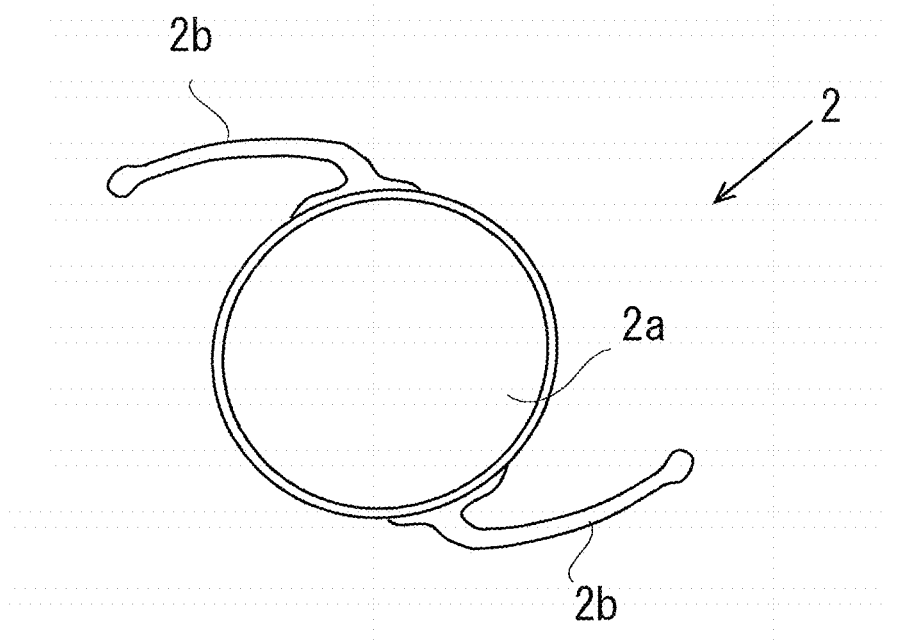
FIG. 2A is a diagram schematically illustrating a configuration of an intraocular lens according to one embodiment.
Figure 2B:
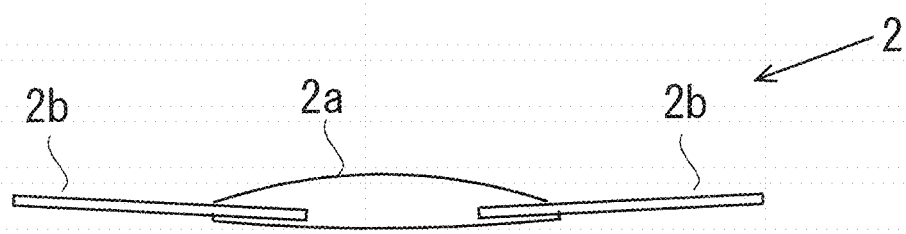
FIG. 2B is another diagram schematically illustrating a configuration of an intraocular lens according to one embodiment.

FIGS. 2A and 2B are diagrams schematically illustrating the configuration of the intraocular lens 2. FIG. 2A is a diagram illustrating a plan view, and FIG. 2B is a diagram illustrating a side view. The intraocular lens 2 is what is called a one-piece type intraocular lens. Although it is assumed in the following descriptions that the intraocular lens 2 is the one-piece type intraocular lens, the present embodiment is also applicable to what is called a three-piece type or a plate type intraocular lens instead of the one-piece type intraocular lens. The intraocular lens 2 is formed of the lens body 2a having a predetermined refractivity, and two plate-like support members 2b which are connected to the lens body 2a and are provided for holding the lens body 2a inside of the eyeball.

FIG. 3 is a plan view of the nozzle body 10. As illustrated in FIGS. 1A and 1B as above, in the nozzle body 10, the intraocular lens 2 is set on the stage member 12. In such a state, the intraocular lens 2 is pushed by the plunger 30, and is ejected from the distal end member 10a. Here, a through-hole 10c whose cross-sectional shape becomes smaller toward the distal end of the nozzle body 10 corresponding to a change that a profile of the nozzle body 10 becomes thinner toward the distal end of the nozzle body 10 is formed inside of the nozzle body 10. Although the cross section of the through-hole is illustrated as an oval shape (egg shape) in the diagrams, the shape of the cross section of the through-hole can be changed to a circle shape or an ellipse shape according to the shape of the specification of an intraocular lens. It is noted that the through-hole is an example of a path of an insertion used for inserting an intraocular lens into the eyeball. When the intraocular lens 2 is ejected from the distal end member 10a, the intraocular lens 2 is deformed corresponding to a change in a cross-sectional shape of the through-hole 10c formed inside of the nozzle body 10, and is ejected after being deformed into a shape which facilitates the entrance of the intraocular lens 2 into the incision formed in the eyeball of the patient.

The distal end member 10a has what is called a bevel-cut shape, which is an obliquely cut shape, such that an upper region of the nozzle body 10 extends more toward a front side than a lower region of the nozzle body 10. The bevel-cut shape distal end member 10a may be formed by obliquely cutting the distal end member 10a so as to have a straight line shape as viewed from a lateral direction or may be formed by obliquely cutting the distal end member 10a so as to have an outwardly bulging shape or a curved surface shape.

A stage groove 12a having a width slightly larger than a diameter of the lens body 2a of the intraocular lens 2 is formed on the stage member 12. The size of the stage groove 12a in the longitudinal direction is set larger than the total size of the intraocular lens 2 including the support members 2b, 2b extending from both sides of the intraocular lens 2. A setting surface 12b is formed of a bottom surface of the stage groove 12a. The position of the setting surface 12b in a vertical direction is set higher than the height position of a bottom surface of the through-hole 10c formed in the nozzle body 10, and the setting surface 12b and the bottom surface of the through-hole 10c are connected to each other by a bottom member inclined surface 10d.

The stage member 12 and the stage lid member 13 are integrally formed with each other. The size of the stage lid member 13 in the longitudinal direction is set substantially equal to the size of the stage member 12 in the longitudinal direction. The stage lid member 13 is connected to the stage member 12 by a thin-plate-like connecting member 14 which is formed in an extending manner toward the stage lid member 13 from a side surface of the stage member 12. The connecting member 14 is formed in a bendable manner at a center portion thereof, and the stage lid member 13 overlaps with the stage member 12 from above by bending the connecting member 14 so that the stage lid member 13 is closed.

In the stage lid member 13, ribs 13a and a rib 13b for reinforcing the stage lid member 13 and for stabilizing the position of the intraocular lens 2 are formed on the surface of the stage lid member 13 which faces the setting surface 12b in a lid closed state. In addition, guide projections 13c are formed on the stage lid member 13 as an upper guide for the plunger 30. Further, the insertion hole 13d is formed in the stage lid member 13 and the insertion hole 13d is used for providing viscoelastic material for the intraocular lens 2 with the stage lid member 13 closed. The viscoelastic material is an example of a lubricant for facilitating the move of the intraocular lens 2 to the distal end member 10a of the nozzle body 10. Hyaluronic acid is commonly used as the viscoelastic material.

Figure 4A:
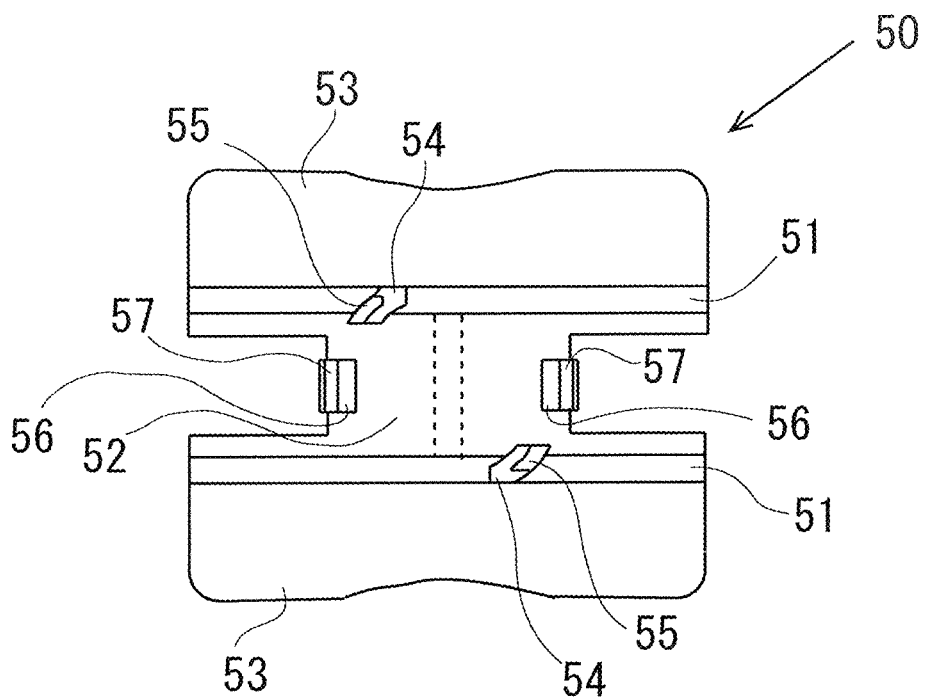
FIG. 4A is a diagram schematically illustrating a configuration of a positioning member according to one embodiment.
Figure 4B:
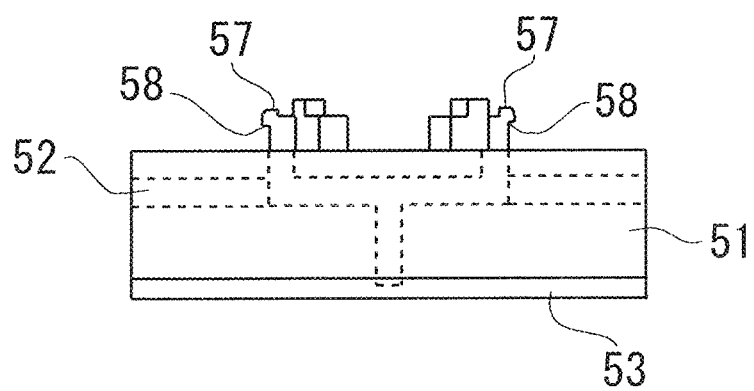
FIG. 4B is another diagram schematically illustrating a configuration of a positioning member according to one embodiment.

The positioning member 50 is detachably mounted on a lower side of the setting surface 12b of the stage member 12. FIGS. 4A and 4B illustrate a schematic configuration of the positioning member 50. FIG. 4A is a plan view of the positioning member 50, and FIG. 4B is a left side view of the positioning member 50. The positioning member 50 is formed as a body separate from the nozzle body 10, and is configured such that a pair of side wall members 51 is connected to each other by a connecting member 52. Retaining members 53 which extend and expand outwardly are formed on lower ends of the side wall members 51.

A pair of the first placing members 54 which has an arcuate shape as viewed from above and projects upward is formed on the upper end portions of the respective side wall members 51. The first positioning members 55 are formed on the outer peripheral sides of the upper end surfaces of the first placing members 54 in a projecting manner. The distance between the inner arcuate peripheral sides of the first positioning members 55 is set slightly larger than the diameter of the lens body 2a of the intraocular lens 2.

A pair of second placing members 56 which has a rectangular shape as viewed from above and projects upward is formed on both ends of the connecting member 52 in the longitudinal direction. The height of the upper surfaces of the second placing members 56 is set to be substantially equal to the height of the upper surfaces of the first placing members 54. Second positioning members 57 which project further upward are formed on the outer portions of the upper surfaces of the second placing members 56 such that the second positioning members 57 extend over the whole regions of the second placing members 56 in the lateral direction. The distance between the inner sides of the second positioning members 57 is set slightly larger than the diameter size of the lens body 2a of the intraocular lens 2. In addition, engaging pawls 58 which project slightly in the longitudinal direction respectively are formed on the upper end portions of the second placing members 56 such that the engaging pawls 58 extend over the whole region of the second placing members 56 in the lateral direction.

The above-mentioned positioning member 50 is assembled to the nozzle body 10 from below the setting surface 12b of the nozzle body 10. The setting surface through-holes 12c which penetrate the setting surface 12b in the thickness direction are formed in the setting surface 12b of the nozzle body 10. The profiles of the setting surface through-holes 12c have a shape slightly larger than and substantially similar to the shape of the first placing members 54 and the shape of the second placing members 56 of the positioning member 50 as viewed from above. When the positioning member 50 is mounted on the nozzle body 10, the first placing members 54 and the second placing members 56 are inserted into the setting surface through-holes 12c from below the setting surface 12b, and project upward from the setting surface 12b.

At this stage of the operation, the engaging pawls 58 respectively formed on the second positioning members 57 project from the setting surface 12b through the setting surface through-holes 12c, and are engaged with the upper surface of the setting surface 12b. With such a configuration, the positioning member 50 is assembled to the nozzle body 10 from below, and the first placing members 54 and the second placing members 56 are fixed to the setting surface 12b in a state where the first placing members 54 and the second placing members 56 project from the setting surface 12b. When the intraocular lens 2 is set on the setting surface 12b, the bottom surface of the outer peripheral portion of the lens body 2a is placed on the upper surfaces of the first placing members 54 and the upper surfaces of the second placing members 56. The position of the lens body 2a in the horizontal direction (the direction horizontal to the setting surface 12b) is restricted by the first positioning members 55 and the second positioning members 57.

When the intraocular lens insertion apparatus 1 is used to insert the intraocular lens 2 into the eyeball, firstly, hyaluronic acid which is a lubricant necessary for the intraocular lens 2 to move in the nozzle body 10 is injected into the area where the hyaluronic acid is necessary by inserting a needle of an injection syringe through the distal end member 10a of the nozzle body 10 or the insertion hole 13d. When the necessary amount of hyaluronic acid is injected, the positioning member 50 is detached from the nozzle body 10. With such an operation, the first placing members 54 and the second placing members 56 which support the lens body 2a of the intraocular lens 2 are retracted from the setting surface 12b, and the intraocular lens 2 is placed on the setting surface 12b in a movable manner. And the user pushes the plunger 30 to move the intraocular lens 2 to a predetermined position.

Next, the user inserts the distal end member 10a of the nozzle body 10 through the incision produced in the ophthalmic tissue of the eyeball. With this operation, the positional relationship between the distal end member 10a and the incision is determined. After the distal end member 10a of the nozzle body 10 is positioned with respect to the incision, the user pushes the pushing plate member 33 of the plunger 30 toward the distal end of the nozzle body 10. As a result, the distal end of the operating member 31 of the plunger comes into contact with the lens body 2a of the intraocular lens 2 set on the setting surface 12b, and the intraocular lens 2 is guided toward the distal end member 10a by the plunger 30.

FIGS. 5A and 5B illustrate the schematic configuration of the plunger 30. A longitudinal length of the plunger 30 is set slightly larger than the longitudinal length of the nozzle body 10. The plunger 30 is formed of: an operating member 31 which is disposed on a distal end side and basically has a columnar shape; and an insertion member 32 which is disposed on a rear end side and basically has a rectangular rod shape. The operating member 31 is configured to include a columnar member 31a having a columnar shape and thin-plate-shaped flat members 31b expanding in the lateral direction from the columnar member 31a.

A notch member 31c is formed on the distal end portion of the operating member 31. As illustrated in FIG. 5A, the notch member 31c is formed on the operating member 31 in a groove shape such that the notch member 31c opens upward and penetrates the operating member 31 in the lateral direction. As can be understood from FIG. 5B, a groove wall disposed on the distal end side of the notch member 31c is formed of an inclined surface which extends upward as the inclined surface extends toward the distal end side of the operating member 31. On the other hand, the insertion member 32 has an approximately H-shaped cross section as a whole, and the size of the insertion member 32 in the lateral direction and the size of the insertion member 32 in the vertical direction are set slightly smaller than those of the through-hole 10c formed in the nozzle body 10. In addition, a disc-shaped pushing plate member 33 which expands in the vertical direction as well as in the lateral direction is formed on a rear end of the insertion member 32.

A pawl member 32a which projects toward the upper side of the insertion member 32 and is vertically movable due to elasticity of the material of the plunger 30 is formed on a portion of the insertion member 32 ranging from the distal end to the center in the longitudinal direction. When the plunger 30 is inserted into the nozzle body 10, an engaging hole 10e illustrated in FIG. 3 which is formed in the upper surface of the nozzle body 10 in the thickness direction and the pawl member 32a are engaged with each other. With such engagement, the relative position between the nozzle body 10 and the plunger 30 in the initial state is determined. The position where the pawl member 32a is formed and the position where the engaging hole 10e is formed are set such that, in an engaging state, the distal end of the operating member 31 is positioned behind the lens body 2a of the intraocular lens 2 set on the stage member 12, and the support members 2b on the rear side of the lens body 2a can be supported by the notch member 31c from below.

Before the intraocular lens 2 is accommodated in the intraocular lens insertion apparatus 1 having the above-mentioned configuration, the plunger 30 is arranged at an initial position in a state where the plunger 30 is inserted into the nozzle body 10. As described previously, the positioning member 50 is attached to the nozzle body 10 from below the setting surface 12b. With such a configuration, the first placing members 54 and the second placing members 56 of the positioning member 50 are held in a projecting manner from the setting surface 12b.

Next, the lens body 2a of the intraocular lens 2 is placed and positioned on the upper surfaces of the first placing members 54 and the upper surfaces of the second placing members 56 in a state where the support members 2b are directed in the longitudinal direction of the nozzle body 10. In such a state, a part of the support member 2b on the rear side of the intraocular lens 2 is tucked by the notch member 31c of the plunger 30 and is supported by the bottom surface of the notch member 31c of the plunger 30.

Figure 6A:
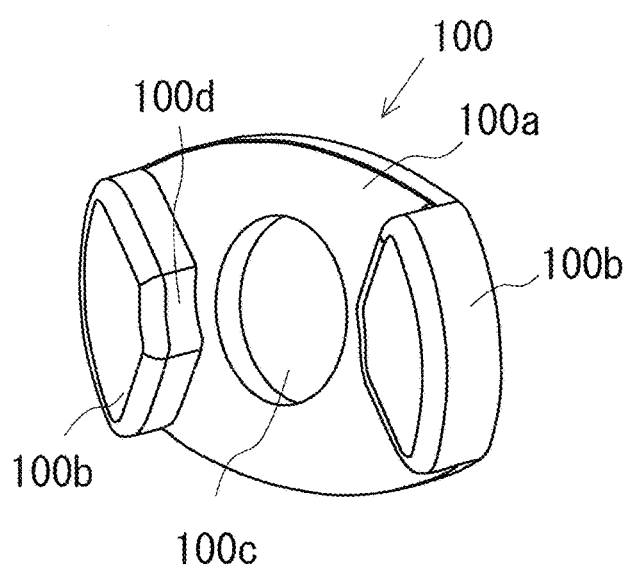
FIG. 6A is a diagram schematically illustrating a configuration of an operability enhancing member according to one embodiment.
Figure 6B:
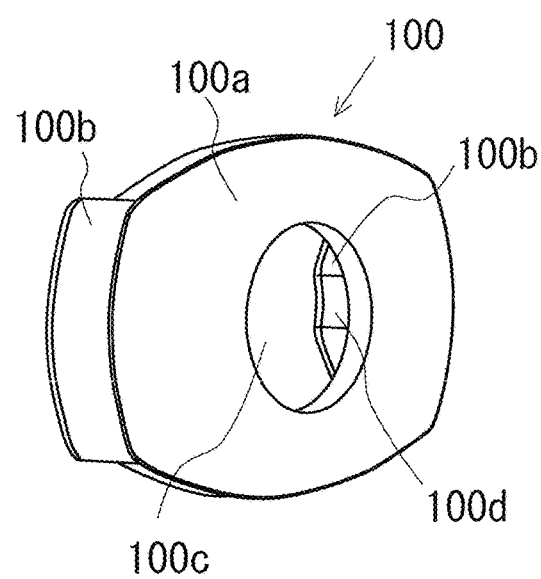
FIG. 6B is another diagram schematically illustrating a configuration of an operability enhancing member according to one embodiment.

Next, the configurations of the hold member 11 of the nozzle body 10 and members connected with the hold member 11 according to the present embodiment are described below. FIGS. 6A and 6B are diagrams schematically illustrating an operability enhancing member 100 attached to the hold member 11 in the present embodiment. As illustrated in FIGS. 6A and 6B, the operability enhancing member 100 includes an engaging plate member 100a and a retaining member 100b. A through-hole 100c is formed in the engaging plate member 100a. The plunger 30 of the intraocular lens insertion apparatus 1 is inserted into the through-hole 100c and the operability enhancing member 100 is attached to the hold member 11. In this case, the upper end and the lower end of the engaging plate member 100a are engaged with the plate members 11a and the engaging members 11b of the hold member, respectively. As a result, the operability enhancing member 100 is fixed to the hold member 11.

When the operability enhancing member 100 is attached to the intraocular lens insertion apparatus 1, it is desirable to achieve that the plunger 30 moves precisely along the axis of the plunger 30 without a tilt. Therefore, when the operability enhancing member 100 is attached to the intraocular lens insertion apparatus 1, it is necessary that the operability enhancing member 100 is not attached to a position deviating from the proper attaching position due to looseness of the attaching (connecting) member and that the operability enhancing member 100 is not tilted about the axis of the plunger 30 due to the looseness thereof. When the operability enhancing member 100 is attached to a position deviating from the proper attaching position or the operability enhancing member 100 is tilted to the direction of the axis of the plunger 30, it may be difficult for the user to push the plunger 30 to the direction of the axis of the plunger 30 or unnecessary force is applied to the plunger 30 to hinder the user's operations since the sliding friction resistance of a slide of the plunger 30 increases unnecessarily.

In the present embodiment, the retaining member 100b of the operability enhancing member 100 is configured to fit with the collar member 11c of the hold member 11 when the operability enhancing member 100 is attached to the hold member 11. Specifically, the lateral wall 100d of the retaining member 100b which is located on the side facing the through-hole 100c comes into contact with the edge of the collar member 11c. As a result, it is expected that a shift of the relative position of the operability enhancing member 100 with respect to the hold member 11 can be prevented when the operability enhancing member 100 is attached to the hold member 11. It is noted that the retaining member 100b is an example of a tilt prevention mechanism. In addition, at least a concave-convex fitting member such that a concave part of the concave-convex fitting member is formed on a part of either the operability enhancing member 100 or the intraocular lens insertion 1 and a convex part of the concave-convex fitting member is formed on a corresponding part of the other functions to prevent the shift of the relative position of the operability enhancing member 100 with respect to the hold member 11 and/or the tilt thereof when the operability enhancing member 100 is attached to the intraocular lens insertion apparatus 1. With the above configuration, the operability enhancing member 100 can be attached to the intraocular lens insertion apparatus 1 more easily and more precisely than other members without the above configurations.

Figure 6C:
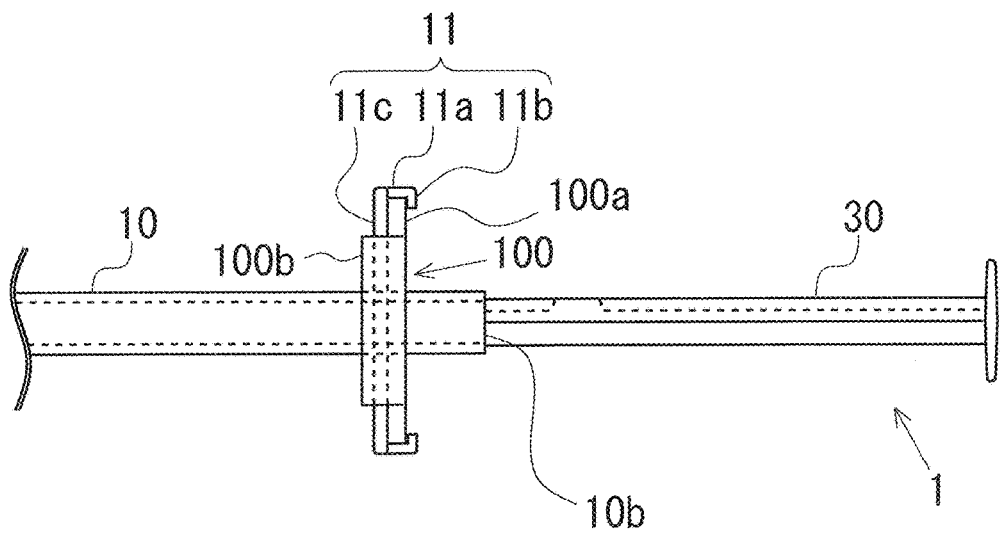
FIG. 6C is a diagram schematically illustrating an operability enhancing member attached to an intraocular lens insertion apparatus.

FIG. 6C schematically illustrates that the operability enhancing member 100 as illustrated in FIGS. 6A and 6B is attached to the intraocular lens insertion apparatus 1. When the operability enhancing member 100 is attached to the intraocular lens insertion apparatus 1, the plunger 30 is inserted through the through-hole 100c of the operability enhancing member 100 from the rear end side of the intraocular lens insertion apparatus 1. In addition, a part of the rear end member 10b of the nozzle body 10 is inserted through the through-hole 100c of the operability enhancing member 100. Further, the operability enhancing member 100 is attached to the hold member 11 since the engaging plate member 100a of the operability enhancing member 100 is engaged with the engaging member 11b of the hold member 11. Moreover, as another way of attaching the operability enhancing member 100 to the intraocular lens insertion apparatus 1, a concave member is provided on a part of the outer wall of the intraocular lens insertion apparatus 1 and a protrusion which can be engaged with the concave member is provided for a part of the operability enhancing member 100.

The hold member 11 of the intraocular lens insertion apparatus 1 according to the present embodiment extends in the upward direction and the downward direction from the nozzle body 10. Therefore, when the user hooks his finger to the hold member 11 for handling the plunger 30 to insert the intraocular lens 2 into the eyeball of the patient, the user might feel awkward in holding the intraocular lens insertion apparatus 1. However, since the operability enhancing member 100 is attached to the hold member 11 in the present embodiment, the user can hook his finger onto the hold member 11 and the operability enhancing member 100. As a result, the user can hold the intraocular lens insertion apparatus 1 more stably than conventional intraocular lens insertion apparatuses. An additional plate member and/or an additional engaging member can be provided for a part facing the retaining member 100b (that is the rearward direction) on the engaging plate member 100a to fix an operability enhancing member according to an embodiment described later.

Although the present embodiment is described as above, the configurations of the intraocular lens insertion apparatus are not limited to those as described above and various variations may be made to the embodiment described herein within the technical scope of the above embodiment. Modifications of the above-mentioned embodiment are exemplified hereinafter. In the description made hereinafter, respective constitutional elements corresponding to the constitutional elements of the above-mentioned embodiment are given the same symbols, and the repeated description of the constitutional elements is omitted unless otherwise specified.

Second Embodiment

Figure 7A:
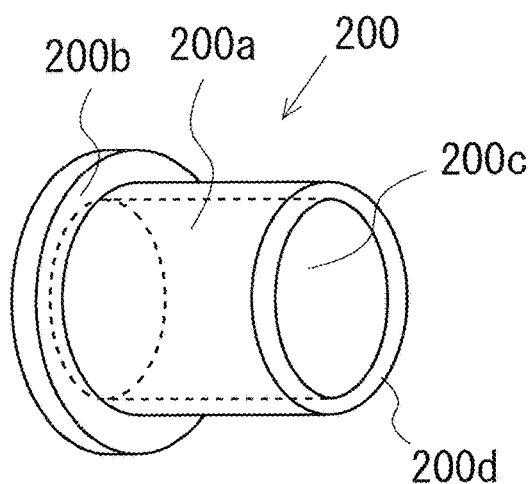
FIG. 7A is yet another diagram schematically illustrating a configuration of an operability enhancing member according to one embodiment.
Figure 7B:
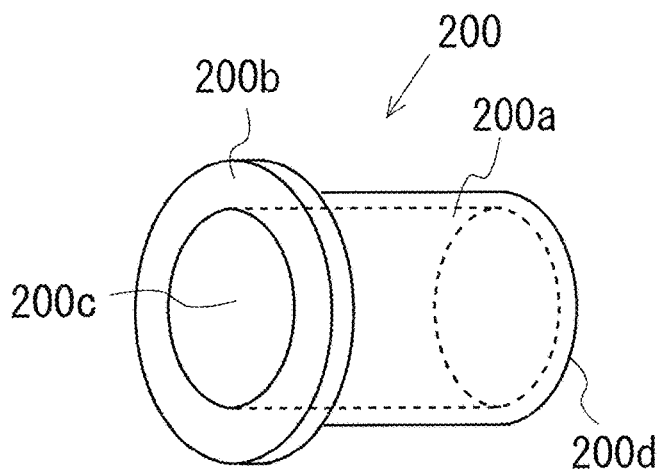
FIG. 7B is still another diagram schematically illustrating a configuration of an operability enhancing member according to one embodiment.
Figure 7C:
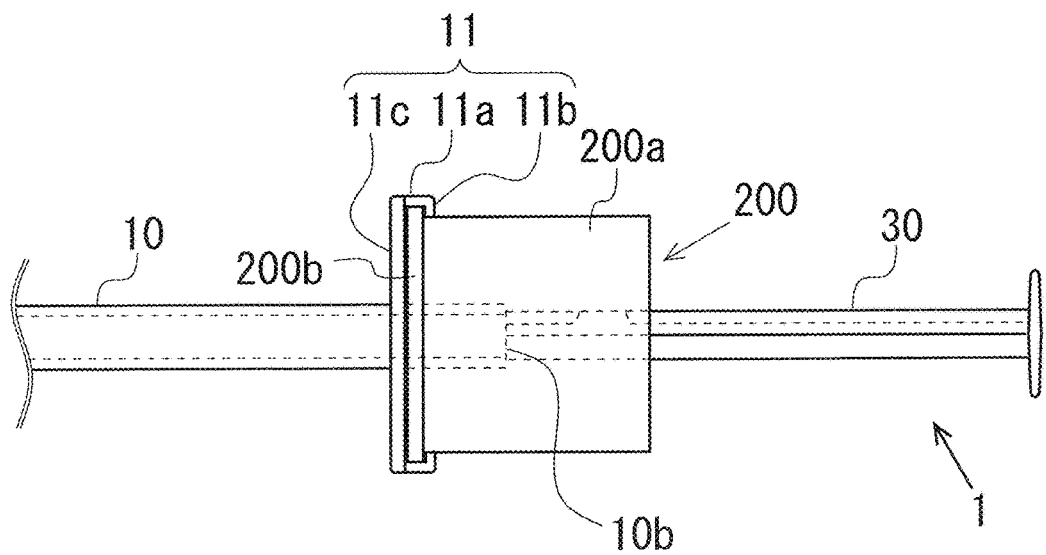
FIG. 7C is a still further diagram schematically illustrating an operability enhancing member attached to an intraocular lens insertion apparatus.

FIGS. 7A, 7B and 7C schematically illustrate an operability enhancing member 200 according to the second embodiment. As illustrated in FIGS. 7A and 7B, the operability enhancing member 200 includes a cylindrical member 200a the shape of which is a hollow cylinder and a flange 200b the shape of which is a ring. The cylindrical member 200a and the flange 200b include an through-hole 200c with a diameter similar to each other, respectively. It is noted that the cylindrical member 200a is an example of a wall part which projects from the rear end of the hook member and beyond the rear end of the apparatus body in a direction opposite to the moving direction of the plunger.

FIG. 7C illustrates that the operability enhancing member 200 as illustrated in FIGS. 7A and 7B is attached to the intraocular lens insertion apparatus 1. When the operability enhancing member 200 is attached to the intraocular lens insertion apparatus 1, the plunger 30 is inserted through the through-hole 200c of the operability enhancing member 200 from the rear end side of the intraocular lens insertion apparatus 1. In addition, a part of the rear end member 10b of the nozzle body 10 is inserted through the through-hole 200c of the operability enhancing member 200.

And each of the upper end part and the lower end part of the flange 200b is engaged with the plate member 11a and the engaging member 11b of the hold member 11. Since the hold member 11 is formed of synthetic resin, the plate member 11a can curve in the upward direction and the downward direction. Therefore, the gap between the engaging members 11b can be widen and narrowed. Further, when the hold member 11 is formed of metal etc. and is formed into a thin plate member, the hold member 11 can curve in the upward direction and the downward direction as is the case with the hold member which is formed of the synthetic resin. Thus, the user curves the plate member 11a to widen the gap between the engaging members 11b so that the user moves the flange 200b through the engaging members 11b to be housed in the hold member 11. When the user allows the shape of the plate member 11a to return to the original shape, the position of the flange 200b is tucked by the plate members 11a, the engaging members 11b and the collar member 11c. As a result, the operability enhancing member 200 is fixed to the hold member 11. In addition, a notch with an opening the diameter of which is larger than the width of the engaging member 11b in the rightward direction and the leftward direction can be provided for a part of the flange 200b. When the flange 200b come into contact with the collar member 11c, the user rotates the flange 200b to allow the engaging member 11b to move through the opening and therefore the operability enhancing member 200 can be fixed to the hold member 11.

When the user pushes the plunger 30 toward the side of the nozzle body 10 with the operability enhancing member 200 attached to the hold member 11 of the intraocular lens insertion apparatus 1, the user's finger come into contact with the rear end part 200d of the cylindrical member 200a of the operability enhancing member 200. Therefore, the movement of the user's finger pushing the plunger 30 can be controlled by the cylindrical member 200a of the operability enhancing member 200. Thus, when the user uses the intraocular lens insertion apparatus 1 according to the present embodiment, the user can handle the plunger 30 to insert the intraocular lens 2 into the eyeball of the patient without a concern that the user pushes the plunger 30 beyond an expected position. As a result, the movement of the plunger 30 can be preferably controlled not to project from the distal end member 10a. A structure configured to contact with the plunger 30 can be provided for the inner surface of the cylindrical member 200a in order to increase the resistive force caused by pushing the plunger to provide an operation feeling for the user.

Third Embodiment

Figure 8A:
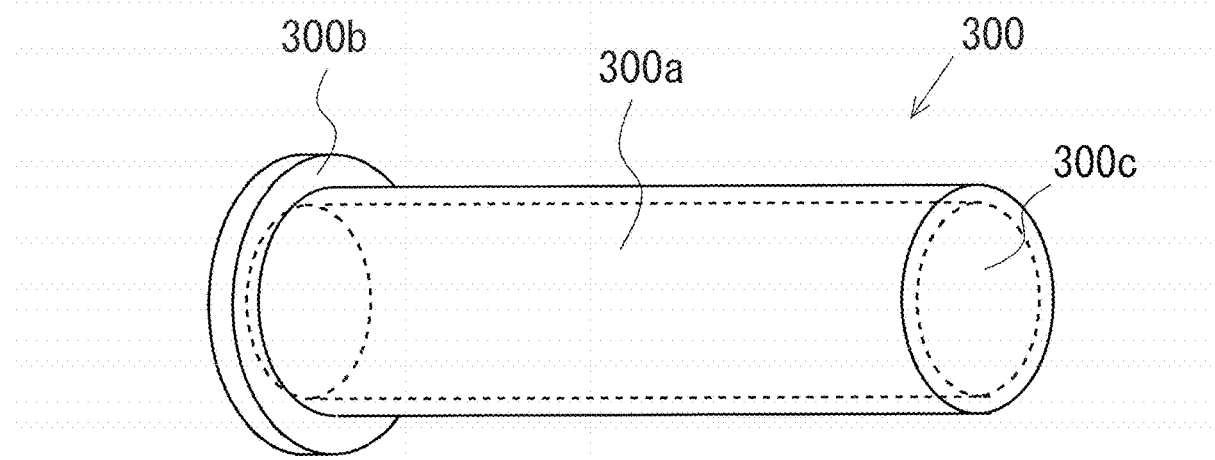
FIG. 8A is a further diagram schematically illustrating a configuration of an operability enhancing member according to one embodiment.
Figure 8B:
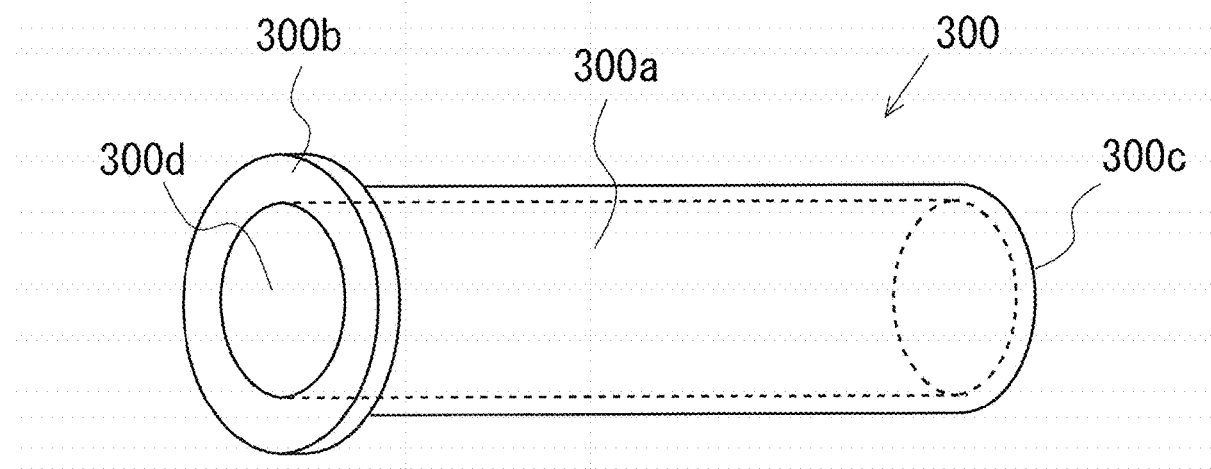
FIG. 8B is a still further diagram schematically illustrating a configuration of an operability enhancing member according to one embodiment.
Figure 8C:
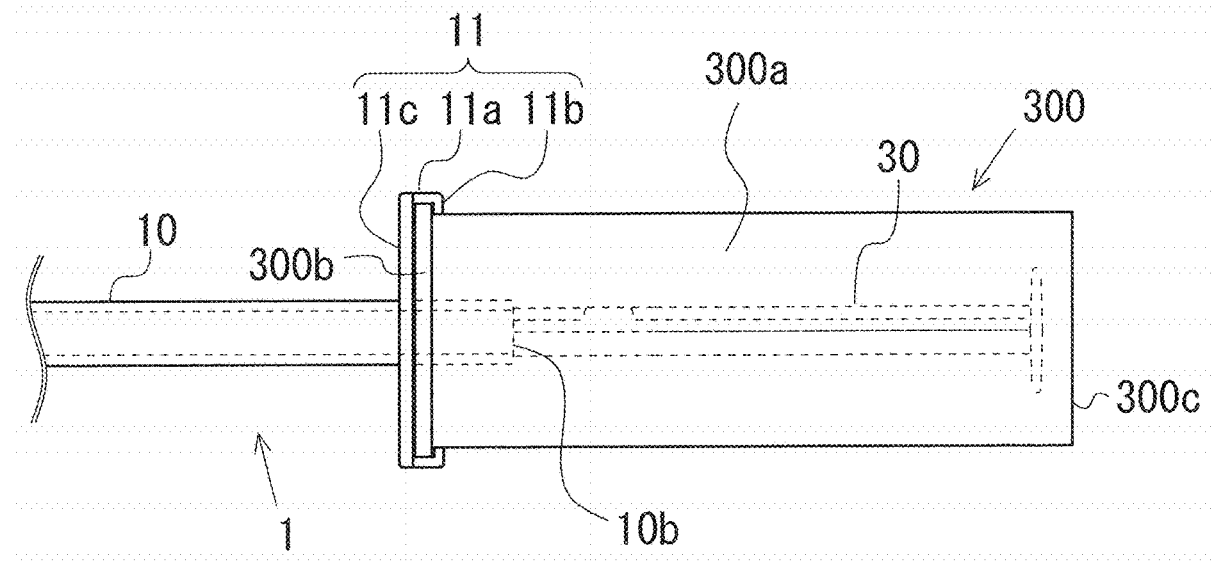
FIG. 8C is a yet further diagram schematically illustrating an operability enhancing member attached to an intraocular lens insertion apparatus.

FIGS. 8A, 8B and 8C schematically illustrate an operability enhancing member 300 according to the third embodiment. As illustrated in FIGS. 8A and 8B, the operability enhancing member 300 includes a hollow cylindrical member 300a, a ring-shaped flange 300b and a wall member 300c. The length of the cylindrical member 300a in the longitudinal direction thereof is configured to be a length with which the wall member 300c does not contact with the plunger 30 when the operability enhancing member 300 is attached to the hold member 11 for transporting or storing the intraocular lens insertion apparatus 1. Each of the cylindrical member 300a and the flange 300b includes a through-hole 300d with a similar diameter. It is noted that the cylindrical member 300a is an example of a tube member which covers the plunger and which extends from the rear end of the hook member in the direction opposite to the direction in which the plunger moves.

FIG. 8C schematically illustrates that the operability enhancing member 300 illustrated in FIGS. 8A and 8B is attached to the intraocular lens insertion apparatus 1. When the operability enhancing member 300 is attached to the intraocular lens insertion apparatus 1, the plunger 30 is inserted from the rear end side of the intraocular lens insertion apparatus 1 through the through-hole 300d of the operability enhancing member 300. In addition, a part of the rear end member 10b of the nozzle body 10 is inserted through the through-hole 300d of the operability enhancing member 300. Similar to the second embodiment as above, each of the upper end member and the lower end member of the flange 300b are engaged with the plate members 11a and the engaging members 11b of the hold member 11 in the present embodiment. As a result, the operability enhancing member 300 is fixed to the hold member 11.

When the operability enhancing member 300 is attached to the hold member 11 of the intraocular lens insertion apparatus 1, the plunger 30 is covered with the cylindrical member 300a and the wall member 300c of the operability enhancing member 300. Therefore, when the intraocular lens insertion apparatus 1 is transported or stored with the operability enhancing member 300 attached to the intraocular lens insertion apparatus 1, the plunger 30 can be prevented from being pushed to the nozzle body 10 unexpectedly to move the intraocular lens 2 housed in the intraocular lens insertion apparatus 1. In addition, it can be expected to prevent in the present embodiment the user unintentionally from operating the plunger 30 when the user handles the intraocular lens insertion apparatus 1.

Fourth Embodiment

Figure 9:
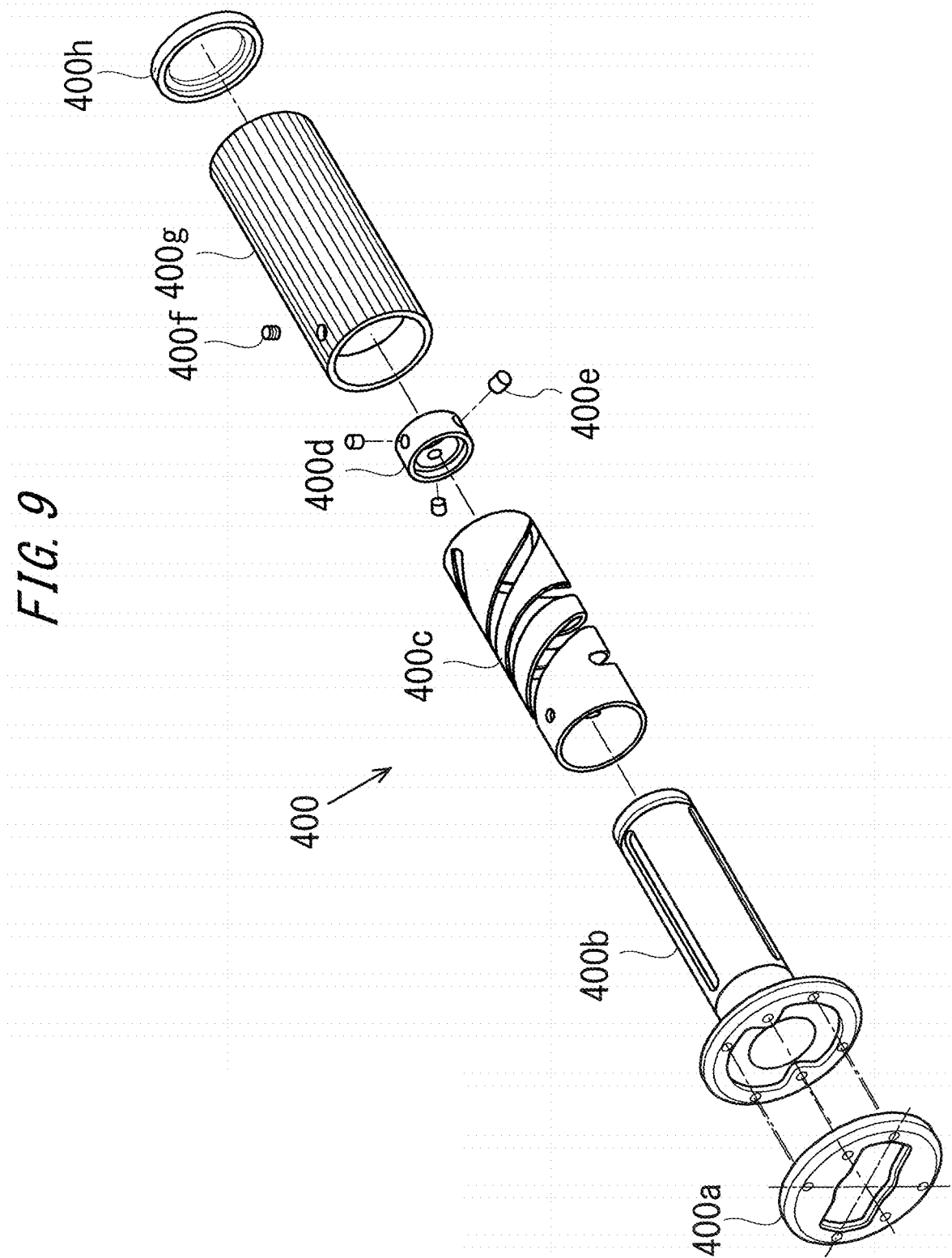
FIG. 9 is a diagram schematically illustrating a configuration of an operability enhancing member according to one embodiment.

FIGS. 9 and 10 schematically illustrate an operability enhancing member 400 according to the fourth embodiment. It is noted that the operability enhancing member 400 is an example of a motion conversion device which converts the rotational motion of a rotating member rotated by the user to a linear motion and transmits the linear motion to the plunger to move in the intraocular lens insertion apparatus. The operability enhancing member 400 includes a front cover 400a, a linear cam tube 400b as a linear cam cylindrical member, a spiral cam tube 400c as a spiral cam cylindrical member, a moving tube 400d as a moving member, a rotating tube 400g as a rotating tube member and a rotating member and a back cover 400h as a rear end supporting member. The front cover 400a is a member the shape of which is approximately disc-shaped and which is configured to engage with the hold member 11 of the intraocular lens insertion apparatus 1. In addition, the plunger 30 is inserted through a hole provided for the front cover 400a.

The linear cam tube 400b includes a tube member the of which is cylindrical and a collar member. Linear holes extending in parallel with the longitudinal axis of the linear cam tube 400b are formed on the cylindrical tube surface of the tube member. In addition, holes through which the plunger 30 is inserted are formed on the collar member. Further, spiral holes are formed on the spiral cam tube 400c. Moreover, the spiral cam tube 400c encompasses the tube member of the linear cam tube 400b. And the spiral cam tube 400c is configured to rotate around the tube member of the linear cam tube 400b.

Additionally, the moving tube 400d is a cylindrical member with the length in the longitudinal direction shorter than the outside diameter thereof. And the inside diameter of the moving tube 400d is configured to decrease stepwise in the longitudinal direction. The parts at which the inside diameter decreases stepwise are configured to contact with the plunger 30. Further, cam pins 400e are fixed to the outer surface of the moving tube 400d. The moving tube 400d is inserted into the inside of the tube member of the linear cam tube 400b and the spiral cam tube 400c. The cam pins 400e are configured to insert into both of the holes of the linear cam tube 400b and the spiral holes of the spiral cam tube 400c.

The rotating tube 400g is a cylindrical member and the inside diameter of the rotating tube 400g is slightly larger than the outside diameter of the spiral cam tube 400c. The rotating tube 400g is fixed to the spiral cam tube 400c by the fixation screw 400f. The back cover 400h is a member the shape of which is approximately disc-shaped. A female screw is formed on the side of the inside diameter of the back cover 400h. The back cover 400h is connected with a male screw of the tube member of the linear cam tube 400b which is formed on the side opposite to the collar member and is fixed to the linear cam tube 400b.

With the configurations as described above, the rotating tube 400g and the spiral cam tube 400c rotate around the tube member of the linear cam tube 400b with the both ends of the rotating tube 400g and the spiral cam tube 400c sandwiched between the collar member of the linear cam tube 400b and the back cover 400h. As a result, the cam pins 400e move linearly in the axis direction along with the holes of the linear cam tube 400b according to the rotation of the spiral holes of the spiral cam tube 400c. Similarly, the moving tube 400d moves linearly in the axis direction. That is, the user can move the moving tube 400d linearly forward and backward in the axis direction by rotating the rotating tube 400g. Consequently, the plunger 30 is pushed toward the nozzle body 10 according to the linear movement of the moving tube 400d.

FIG. 10 schematically illustrates that the operability enhancing member 400 as illustrated in FIG. is attached to the intraocular lens insertion apparatus 1. When the operability enhancing member 400 is attached to the intraocular lens insertion apparatus 1, the plunger 30 is inserted from the rear end of the intraocular lens insertion apparatus 1 through the hole of the front cover 400a of the operability enhancing member 400. In addition, a part of the rear end member 10b of the nozzle body 10 is inserted through the hole of the operability enhancing member 400. As is the case with the second embodiment and the third embodiment, the operability enhancing member 400 is attached to the hold member 11 since the front cover 400a of the operability enhancing member 400 is engaged with the engaging member 11b of the hold member 11.

After the operability enhancing member 400 is attached to the hold member 11 of the intraocular lens insertion apparatus 1, the user rotates the rotating tube 400g of the operability enhancing member 400 to move the plunger 30 toward the side of the nozzle body 10. Thus, when the operability enhancing member 400 is used, the user can perform surgeries without a concern that the user unintentionally pushes the plunger 30 to project from the distal end of the intraocular lens insertion apparatus 1 into an eye of a patient.

The operability enhancing member 400 is configured to convert the rotation move of the rotating tube 400g by the user to the linear move of the moving tube 400d to push the plunger 30. However, the operability enhancing member 400 can be configured to include an electrical driving source such as a motor for rotating the rotating tube 400g instead of the above configuration for moving the plunger 30 by the operability enhancing member 400. Alternately, the operability enhancing member 400 can be configured to include an electrical or fluidic driving source for directly pushing the plunger 30.

Although the present embodiment is described as above, the configurations of the intraocular lens insertion apparatus are not limited to those as described above and various variations may be made to the embodiment described herein within the technical scope of the above embodiment. Variations of the above-mentioned embodiments are exemplified hereinafter. In the description made hereinafter, respective constitutional elements corresponding to the constitutional elements of the above-mentioned embodiments are given the same symbols, and the repeated description of the constitutional elements is omitted unless otherwise specified.

(Variation 1)

FIGS. 11A and 11B schematically illustrate an operability enhancing member and an intraocular lens insertion apparatus according to the variation 1. Although the connecting member is provided for the hold member of the nozzle body in the above embodiments, a connecting member 1012 can be provided on the rear end member 10b of the nozzle body 10 in the intraocular lens insertion apparatus 1000. Similar to the above embodiments, an operability enhancing member 1100 which employs the configuration similar to the operability enhancing member 100 as described above can be attached to the connecting member 1012 as illustrated in FIG. 11A in the present variation. Although the connecting member 1012 can be formed integrally on the nozzle body 10 as illustrated in FIG. 11A, the connecting member 1012 can be attached as a separate member to the nozzle body 10 as illustrated in FIG. 11B.

(Variation 2)

Figure 12:
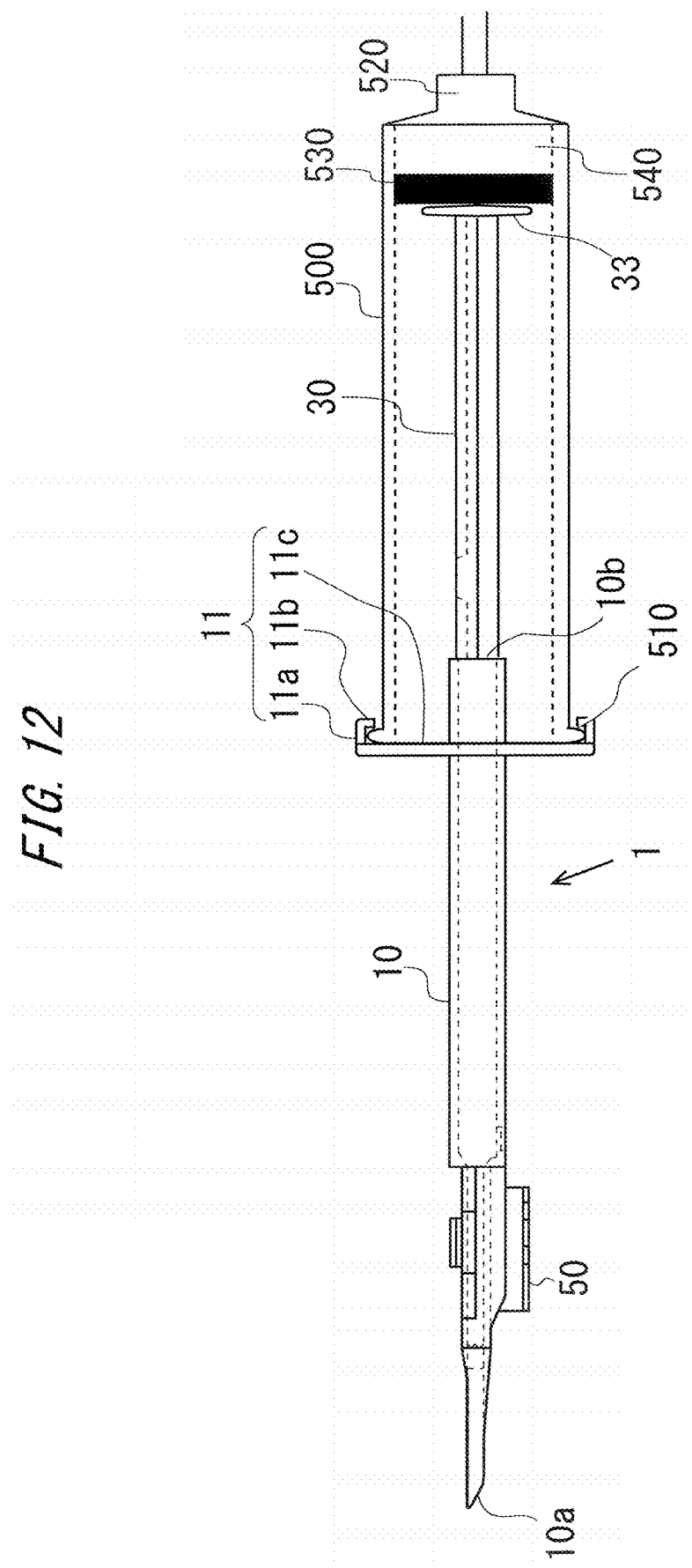
FIG. 12 is a diagram illustrating an intraocular lens insertion apparatus and a syringe 500 according to one variation.

FIG. 12 schematically illustrates the intraocular lens insertion apparatus 1 and a syringe 500 attached to the intraocular lens insertion apparatus 1 according to the variation 2. The syringe 500 includes a flange 510, a connecting member 520 which can be connected with a fluid delivery means (not illustrated) for delivering fluid to the syringe 500 and a piston 530 which is moved by the pressure applied by the fluid. When the fluid delivered to the area 540 between the connecting member 520 and the piston 530 by the fluid delivery member, the piston 530 is moved by the fluid to the side of the distal end member 10a of the nozzle body 10. And when the piston 530 comes into contact with the pushing plate member 33 of the plunger 30 and further moves to the side of the distal end member 10a of the nozzle body 10, the plunger 30 also moves to the side of the distal end member 10a of the nozzle body 10.

(Variation 3)

FIGS. 13A, 13B and 13C schematically illustrate an attaching member 600 which is attached to the intraocular lens insertion apparatus 1 according to the variation 3. The attaching member 600 is an example of a connecting member. The attaching member 600 includes a backboard 600a which is rectangular, two lateral walls 600b which is connected with the backboard 600a on the left edge 600i side and on the right edge 600j side of the backboard 600a and which extends from the upper edge 600h side to the lower edge 600k side, and a baseplate 600c which is connected with the backboard 600a on the lower edge 600k side. A plurality of through-holes 600f are provided for the backboard 600a from the upper edge 600h side down to the lower edge 600k side of the backboard 600a. The through-holes 600f function as an example of a detachment prevention mechanism. In addition, concave members 600g through which the hold member 11 of the nozzle body 10 moves is provided between the lateral walls 600b and the baseplate 600c. Further, a connecting member 600e the configuration of which is similar to the configuration of the combination of the plate member 11a and the engaging member 11b is provided for the baseplate 600c.

FIG. 13C schematically illustrates that the intraocular lens insertion apparatus 1 and the operability enhancing member 200 are attached to the attaching member 600. When the intraocular lens insertion apparatus 1 and the operability enhancing member 200 are attached to the attaching member 600, the hold member 11 of the nozzle body 10 is engaged with the concave member 600g. In addition, the flange 200b of the operability enhancing member 200 is engaged with the connecting member 600e. As a result, the hold member 11 and the flange 200b are fixed to the attaching member 600 by the baseplate 600c and the connecting member 600e. Additionally, when the user tries to detach the hold member 11 or the flange 200b from the attaching member 600 after the hold member 11 and the flange 200b are once fixed to the attaching member 600, a bending rupture of the part including through-holes 600f is caused by the force applied to the attaching member 600. Therefore, reusing of the attaching member 600 which has been once attached to the intraocular lens insertion apparatus 1 can be prevented.

(Variation 4)

FIGS. 14A, 14B, 14C and 14D schematically illustrate an attaching member 700 which is attached to the intraocular lens insertion apparatus 1 according to the variation 4. The configuration of the attaching member 700 is similar to the configuration of the attaching member 600 according to the variation 3 and a concave member 710 is provided for a connecting member 700e corresponding to the connecting member 600e. In addition, an operability enhancing member 800 the configuration of which is similar to the configuration of the operability enhancing member 200 is attached to the attaching member 700. The operability enhancing member 800 includes a wedge-shaped protrusion 810 formed on the outer surface of the cylindrical member 200a which engages with the concave member 710 of the connecting member 700e of the attaching member 700.

FIGS. 14C and 14D schematically illustrate states before and after the intraocular lens insertion apparatus 1 and the operability enhancing member 800 are attached to the attaching member 700, respectively. When the intraocular lens insertion apparatus 1 and the operability enhancing member 800 are attached to the attaching member 700, the hold member 11 of the nozzle body 10 is engaged with the concave member 600g. In addition, the flange 200b of the operability enhancing member 800 is engaged with the connecting member 700e. In this case, the protrusion 810 of the operability enhancing member 800 is engaged with the concave member 710. As a result, the hold member 11 and the flange 200b are fixed to the attaching member 700 by the baseplate 600c and the connecting member 700e. Additionally, the engagement between the protrusion 810 and the concave member 710 can decrease the possibility that the operability enhancing member 800 is detached from the attaching member 700.

In the present variation, the operability enhancing member 800 can be replace with an operability enhancing member 900 as illustrated in FIGS. 15A and 15B. The operability enhancing member 900 includes a plate spring 910 which can be engaged with the concave member 710 instead of the protrusion 810 of the operability enhancing member 800. In this case, as illustrated in FIGS. 15A and 15B, the engagement between the plate spring 910 and the concave member 710 can decrease the possibility that the operability enhancing member 900 is detached from the attaching member 700.

(Variation 5)

FIGS. 16A, 16B and 16C schematically illustrate an attaching member 1200 which is attached to the intraocular lens insertion apparatus 1 according to the variation 5. The configuration of the attaching member 1200 is similar to the configuration of the attaching member 600 according to the variation 3 and a concave member 1200m which can be engaged with the hold member 11 of the nozzle body 10 is provided for a lateral wall corresponding to the lateral wall 600b. In addition, the connecting member 600e of the attaching member 600 is configured to be engaged with the hold member 11 and the flange 200b as described above. However, since the hold member 11 is engaged with the concave member 1200m in the present variation, a connecting member 1200e of the attaching member 1200 is engaged only with the flange 200b. The connecting member 1200e is an example of a first attaching member and the concave member 1200m is an example of a second attaching member.

FIG. 16C schematically illustrates that the intraocular lens insertion apparatus 1 and the operability enhancing member 200 are attached to the attaching member 1200. When the intraocular lens insertion apparatus 1 and the operability enhancing member 200 are attached to the attaching member 1200, the hold member 11 of the nozzle body 10 is engaged with the concave member 1200m. In addition, the flange 200b of the operability enhancing member 200 is engaged with the connecting member 1200e. As a result, the hold member 11 is fixed to the attaching member 1200 by the concave member 1200m and the lateral wall 600b and the flange 200b is also fixed to the attaching member 1200 by the baseplate 600c and the connecting member 1200e.

(Variation 6)

Figure 17A:
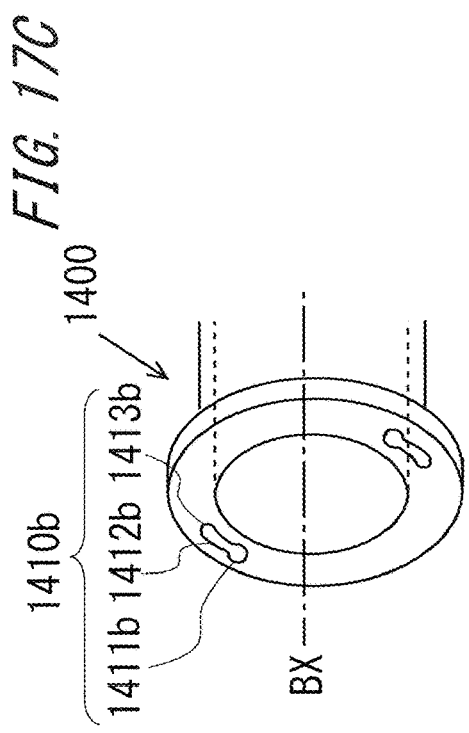
FIG. 17A is a diagram schematically illustrating an intraocular lens insertion apparatus and an operability enhancing member according to a further variation.
Figure 17B:
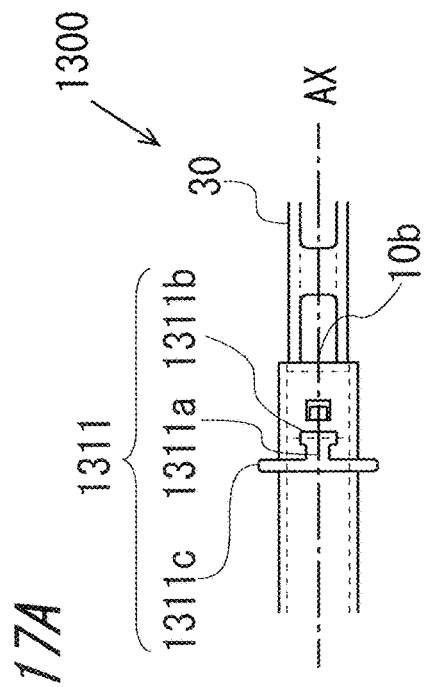
FIG. 17B is another diagram schematically illustrating an intraocular lens insertion apparatus and an operability enhancing member according to a further variation.

FIGS. 17A, 17B, 17C and 17D schematically illustrate an intraocular lens insertion apparatus 1300 and an operability enhancing member 1400 according to the variation 6. The configuration of the intraocular lens insertion apparatus 1300 is similar to the configuration of the intraocular lens insertion apparatus 1 as described above and the hold member 11 of the intraocular lens insertion apparatus 1 is replaced with a hold member 1311. As illustrated in FIGS. 17A and 17B, the hold member 1311 includes a plate member 1311a the configuration of which is similar to the configuration of the plate member 11a, a connecting member 1311b, and a collar member 1311c the configuration of which is similar to the configuration of the collar member 11c. The connecting member 1311b is a protrusion and the cross section of the connecting member 1311b in the plane which is perpendicular to the central axis AX of the plunger 30 is larger than the cross section of the plate member 1311a.

Figure 17C:
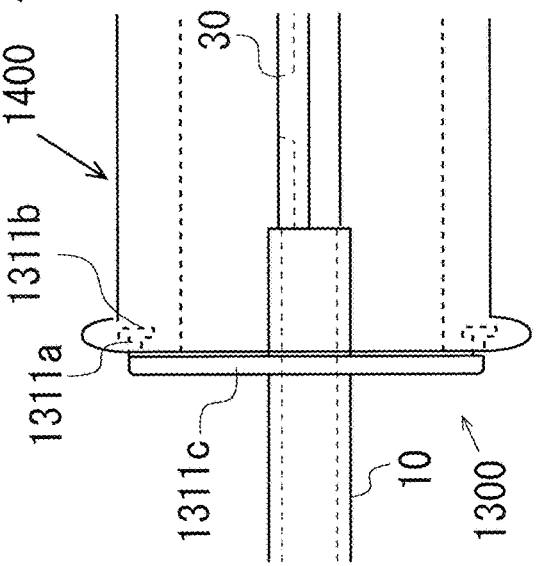
FIG. 17C is yet another diagram schematically illustrating an intraocular lens insertion apparatus and an operability enhancing member according to a further variation.

In the present variation, the connecting member 1311b is connected with a flange 1400b of the operability enhancing member 1400. AS illustrated in FIG. 17C, two connecting grooves 1410b facing each other across the central axis BX of the operability enhancing member 1400 are provided for the flange 1400b. The connecting groove 1410b includes a insertion hole 1411b into which the connecting member 1311b is inserted and a guide groove 1412b for the plate member 1311a connected with the insertion hole 1411b. When the flange 1400b is rotated around the central axis BX after the connecting members 1311b are inserted into the insertion holes 1411b, the plate members 1311a move along the guide grooves 1412b.

Figure 17D:
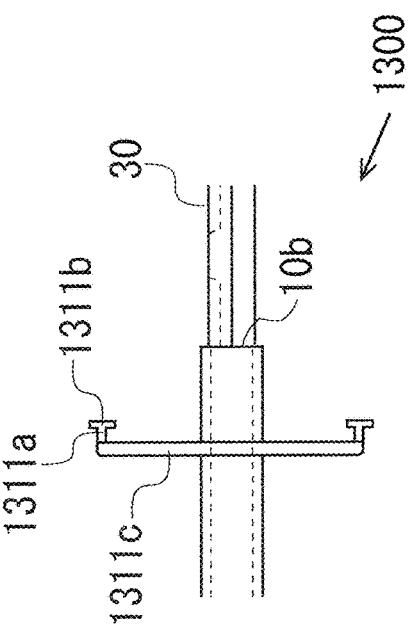
FIG. 17D is still another diagram schematically illustrating an intraocular lens insertion apparatus and an operability enhancing member according to a further variation.

FIG. 17D schematically illustrates that the operability enhancing member 1400 is attached to the intraocular lens insertion apparatus 1300. When the operability enhancing member 1400 is attached to the intraocular lens insertion apparatus 1300, each of the connecting members 1311b is inserted into the counterpart insertion hole 1411b. Next, the flange 1400b is rotates around the central axis BX and the plate members 1311a move along the guide grooves 1412b. When the plate members 1311a come into contact with the end 1413b of the guide grooves 1412b, the rotation of the flange 1400b is stopped. As a result, the flange 200b is fixed to the hold member 1311.

(Variation 7)

Figure 18B:
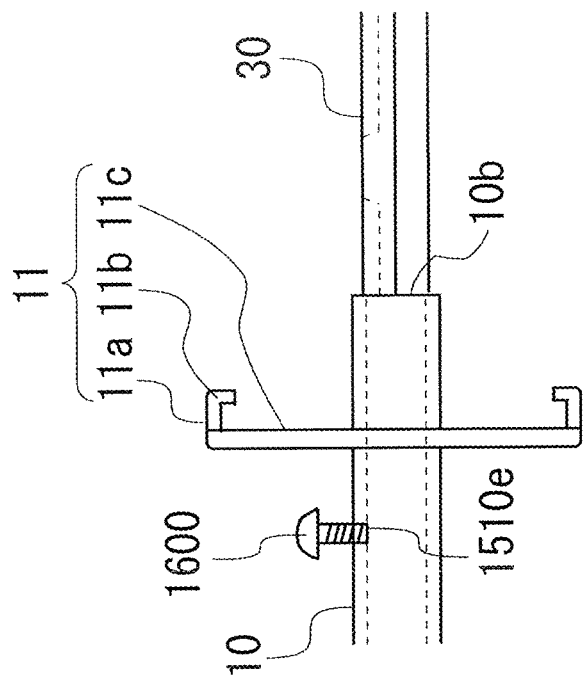
FIG. 18B is another diagram schematically illustrating an intraocular lens insertion apparatus according to a yet further variation.
Figure 18A:
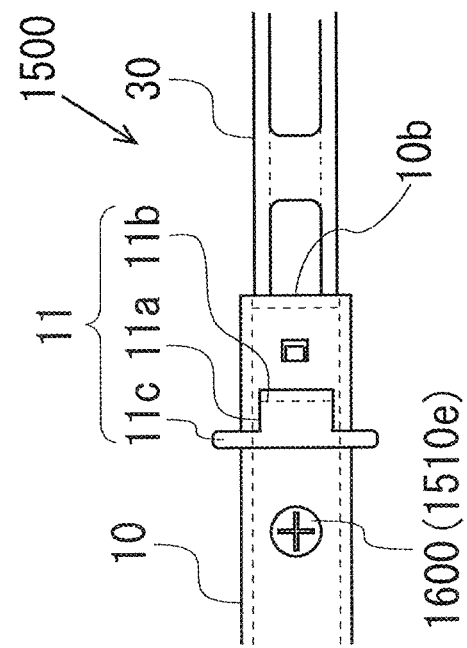
FIG. 18A is a diagram schematically illustrating an intraocular lens insertion apparatus according to a yet further variation.

FIGS. 18A and 18B schematically illustrate an intraocular lens insertion apparatus 1500 according to the variation 7. The configuration of the intraocular lens insertion apparatus 1500 is similar to the configuration of the intraocular lens insertion apparatus 1 as described above. A screw hole 1510e into which a screw 1600 is screwed is provided for the nozzle body 10. As illustrated in FIGS. 18A and 18B, when the screw 1600 is screwed into the screw hole 1510e, the tip of the screw 1600 comes into contact with the plunger 30. As a result, when an operability enhancing member (not illustrated) is attached to the intraocular lens insertion 1500, the screw 1600 prevents undesirable movements of the plunger 30 with respect to the nozzle body 10 caused by the user. In the present variation, when the screw 1600 is unscrewed from the screw hole 1510e after the operability enhancing member is attached to the intraocular lens insertion apparatus 1500, the user can use the intraocular lens insertion apparatus 1500.

A notch which is engaged with the engaging hole 10e can be provided for the plunger 30 instead of the configuration that the screw 1600 is used to prevent undesirable movements of the plunger 30. Alternatively, one end of a tape is attached to the plunger 30, the tape is configured to extend though the engaging hole 10e, and the other end of the tape is located outside the nozzle body 10. In this case, the user pulls the tape from the engaging hole 10e to allow the plunger 30 to move when the user handles the plunger 30.

REFERENCE SIGNS LIST 1 intraocular lens insertion apparatus 2 intraocular lens 10 nozzle body 10a distal end member of nozzle body 10b rear end member of nozzle body 11 hole member 11a plate member 11b engaging member 11c collar member 30 plunger 100, 200, 300, 400 operability enhancing member

What is claimed is:

1. An intraocular lens insertion apparatus comprising:
an apparatus body configured to comprise a housing member for housing an intraocular lens and an insertion tube member for ejecting the intraocular lens into an eyeball of a patient;
a plunger configured to move in the apparatus body; and
a hook member formed on the apparatus body for a user of the intraocular lens insertion apparatus to hook a finger when the user moves the plunger,
wherein the plunger is moved to a side of the insertion tube member, the intraocular lens housed in the housing member is pushed by a distal end of the plunger, and the intraocular lens is ejected from the insertion tube member,
a connector configured to fix an operability enhancer to the hook member of the apparatus body, the operability enhancer is a member for enhancing an operability of the plunger when the plunger is moved with the apparatus body, is provided on the hook member of the apparatus body,
the hook member is formed on the apparatus body and a shape of a part of the hook member is configured to be a plate which is perpendicular to a direction of movement of the plunger, and
the connector comprises a claw which projects toward a posterior side of the apparatus body to connect a flange of the operability enhancer.

2. The intraocular lens insertion apparatus according to claim 1, wherein the connector is integrally formed on the hook member.

3. The intraocular lens insertion apparatus according to claim 1, wherein the connector is detachably formed on the hook member.

4. The intraocular lens insertion apparatus according to claim 1, wherein the operability enhancer is connected to the connector from a rear end side of the apparatus body.

5. The intraocular lens insertion apparatus according to claim 1, wherein the operability enhancer comprises a tilt preventer, which is configured to connect with the connector and which is configured to prevent the direction of movement of the plunger from tilting.

6. The intraocular lens insertion apparatus according to claim 1, wherein the operability enhancer is a plate member configured to increase an area of the hook member onto which the user hooks the finger to move the plunger when the plate member is connected with the connector.

7. The intraocular lens insertion apparatus according to claim 1, wherein the operability enhancer comprises a wall which projects from the rear end of the hook member and beyond the rear end of the apparatus body in a direction opposite to the direction of the movement of the plunger.

8. The intraocular lens insertion apparatus according to claim 1, wherein the operability enhancer comprises a tube member which extends from the rear end of the hook member in a direction opposite to the direction of the movement of the plunger to cover the plunger.

9. The intraocular lens insertion apparatus according to claim 1, wherein the operability enhancer comprises a linear actuator, which is configured to convert a rotational motion of a rotating member rotated by the user to a linear motion and which is configured to transmit the linear motion to the plunger to move in the apparatus body.

10. The intraocular lens insertion apparatus according to claim 1, wherein the operability enhancer comprises a driver configured to move the plunger.

11. The intraocular lens insertion apparatus according to claim 1, wherein the intraocular lens is housed in the housing member before the intraocular lens insertion apparatus is distributed.

12. An intraocular lens insertion apparatus comprising:
an apparatus body configured to comprise a housing member for housing an intraocular lens and an insertion tube member for ejecting the intraocular lens into an eyeball of a patient;
a plunger configured to move in the apparatus body; and
a hook member formed on the apparatus body for a user of the intraocular lens insertion apparatus to hook a finger when the user moves the plunger,
wherein the plunger is moved to a side of the insertion tube member, the intraocular lens housed in the housing member is pushed by a distal end of the plunger, and the intraocular lens is ejected from the insertion tube member,
the intraocular lens insertion apparatus further comprises a connector configured to fix an operability enhancer to the hook member of the apparatus body, the operability enhancer is a member for enhancing an operability of the plunger when the plunger is moved with the apparatus body,
the connector comprises a detachment preventer configured to prevent the operability enhancer and the apparatus body from detaching from the connector after the operability enhancer and the apparatus body are attached to the connector member,
the hook member is formed on the apparatus body and a shape of a part of the hook member is configured to be a plate which is perpendicular to a direction of movement of the plunger, and
the connector comprises a claw which projects toward a posterior side of the apparatus body to connect a flange of the operability enhancer.

13. An intraocular lens insertion apparatus comprising:
an apparatus body configured to comprise a housing member for housing an intraocular lens and an insertion tube member for ejecting the intraocular lens into an eyeball of a patient;
a plunger configured to move in the apparatus body; and
a hook member formed on the apparatus body for a user of the intraocular lens insertion apparatus to hook a finger when the user moves the plunger,
wherein the plunger is moved to a side of the insertion tube member, the intraocular lens housed in the housing member is pushed by a distal end of the plunger, and the intraocular lens is ejected from the insertion tube member,
the intraocular lens insertion apparatus further comprises a connector configured to fix an operability enhancer to the hook member of the apparatus body, the operability enhancer is a member for enhancing an operability of the plunger when the plunger is moved with the apparatus body,
the connector comprises a first attachment to which the operability enhancer is attached and a second attachment to which the hook member is attached, and
the first attachment is located closer to the distal end of the apparatus body than the second attachment when the connector is attached to the intraocular lens insertion apparatus,
the hook member is formed on the apparatus body and a shape of a part of the hook member is configured to be a plate which is perpendicular to a direction of movement of the plunger, and the connector comprises a claw which projects toward a posterior side of the apparatus body to connect a flange of the operability enhancer.

* * * * *